(12) United States Patent
Beaty et al.

(10) Patent No.: US 8,992,750 B1
(45) Date of Patent: Mar. 31, 2015

(54) BIOSENSOR AND METHODS FOR MANUFACTURING

(71) Applicant: Roche Diagnostics Operations, Inc., Indianapolis, IN (US)

(72) Inventors: Terry A. Beaty, Indianapolis, IN (US); Eric R. Diebold, Fishers, IN (US); Abner D. Joseph, Carmel, IN (US); Randall K. Riggles, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/933,697

(22) Filed: Jul. 2, 2013

Related U.S. Application Data

(60) Provisional application No. 61/666,966, filed on Jul. 2, 2012.

(51) Int. Cl.
*G01N 27/00* (2006.01)
*G01N 27/07* (2006.01)
*G01N 27/02* (2006.01)

(52) U.S. Cl.
CPC .................................. *G01N 27/02* (2013.01)
USPC .. 204/403.02; 204/194; 204/400; 204/403.01

(58) Field of Classification Search
USPC ................ 204/193, 194, 400, 403.1–403.15; 205/775, 777.5, 779, 780, 792
See application file for complete search history.

(56) References Cited

U.S. PATENT DOCUMENTS

| | | | |
|---|---|---|---|
| 5,141,868 A | 8/1992 | Shanks et al. | |
| 6,071,391 A | 6/2000 | Gotoh et al. | |
| 6,447,657 B1 | 9/2002 | Bhullar et al. | |
| 6,623,698 B2 | 9/2003 | Kuo | |
| 6,676,995 B2 | 1/2004 | Dick et al. | |
| 6,689,411 B2 | 2/2004 | Dick et al. | |
| 7,144,485 B2 | 12/2006 | Hsu et al. | |
| 7,305,896 B2 | 12/2007 | Howell et al. | |

(Continued)

FOREIGN PATENT DOCUMENTS

| | | |
|---|---|---|
| EP | 1 167 538 A1 | 1/2002 |
| JP | 2007-510155 A | 4/2007 |

(Continued)

OTHER PUBLICATIONS

U.S. Appl. No. 13/712,072 to Riggles, Office Action mailed Sep. 25, 2013.

(Continued)

*Primary Examiner* — Paul Hyun
*Assistant Examiner* — Robert Eom
(74) *Attorney, Agent, or Firm* — Roche Diagnostics Operations, Inc.

(57) ABSTRACT

Embodiments of the invention include a test strip with a sample chamber opening spanning the width of the test strip at the sampling end and including a portion of the lateral sides at that end. The chamber is vertically bounded by upper and lower substrate layers, horizontally bounded by the front face of a spacer layer, and open on the remaining sides. The test strip fills rapidly and requires small sample volumes. Both 1-up and 2-up manufacturing techniques for producing such test strips eliminate registration and alignment steps, and other techniques relating to the 2-up technique (simultaneously manufacturing test strips arranged in multiple columns) are also disclosed.

4 Claims, 24 Drawing Sheets

(56) References Cited

U.S. PATENT DOCUMENTS

| | | |
|---|---|---|
| 7,344,507 B2 | 3/2008 | Briggs et al. |
| 7,476,202 B2 | 1/2009 | Raney et al. |
| 2002/0192115 A1 | 12/2002 | Bhullar et al. |
| 2003/0024811 A1* | 2/2003 | Davies et al. ............ 204/403.01 |
| 2004/0043477 A1 | 3/2004 | Schibli |
| 2005/0019212 A1 | 1/2005 | Bhullar et al. |
| 2005/0103624 A1 | 5/2005 | Bhullar et al. |
| 2005/0247573 A1 | 11/2005 | Nakamura et al. |
| 2007/0040567 A1* | 2/2007 | Popovich et al. ............ 324/765 |
| 2007/0106178 A1 | 5/2007 | Roe et al. |
| 2007/0272563 A1 | 11/2007 | Petyt et al. |
| 2007/0278097 A1 | 12/2007 | Bhullar et al. |
| 2008/0267823 A1 | 10/2008 | Wang et al. |
| 2010/0327886 A1 | 12/2010 | Nakamura et al. |

FOREIGN PATENT DOCUMENTS

| | | |
|---|---|---|
| JP | 2009-543060 A | 12/2009 |
| WO | WO 2004/113901 A1 | 12/2004 |
| WO | WO 2004/113902 A1 | 12/2004 |
| WO | WO 2005/040404 A1 | 5/2005 |
| WO | WO 2008/002837 A2 | 1/2008 |
| WO | WO 2009/042631 A2 | 4/2009 |
| WO | WO 2009/119117 A1 | 10/2009 |

OTHER PUBLICATIONS

International Patent Application PCT/US2011/042574 Corrected International Preliminary Report on Patentability mailed Feb. 11, 2013.

International Patent Application PCT/US2011/042574 International Preliminary Report on Patentability mailed Dec. 13, 2012.

International Patent Application PCT/US2011/042574 International Search Report and Written Opinion mailed Dec. 9, 2011.

International Patent Application PCT/US2011/042574 Second Written Opinion mailed Jul. 17, 2012.

* cited by examiner

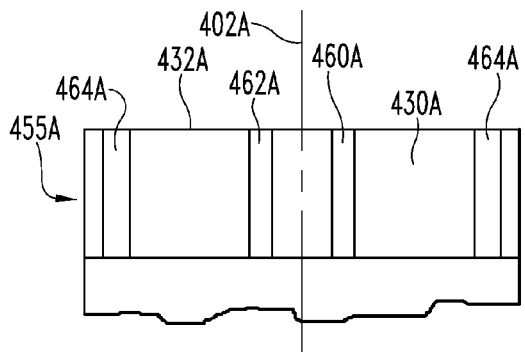
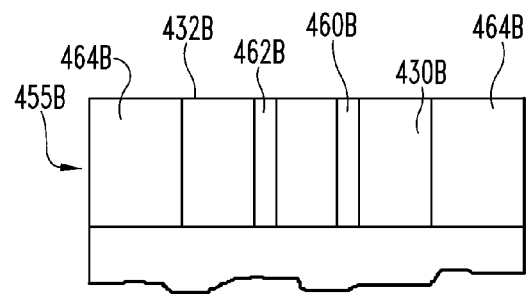
Fig. 26      Fig. 27
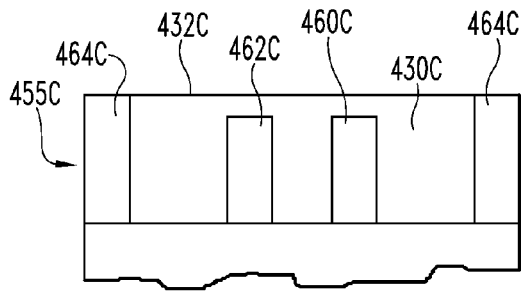
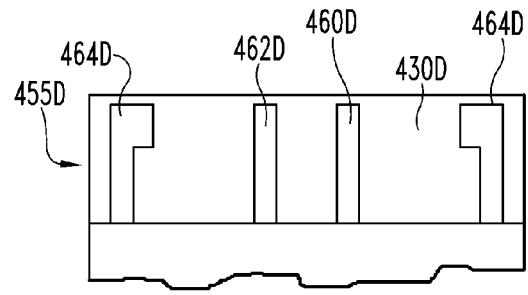
Fig. 28      Fig. 29
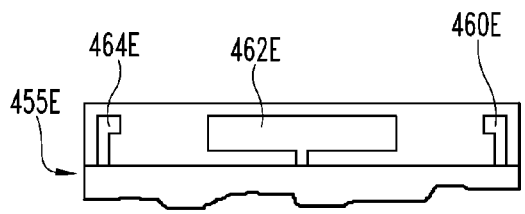
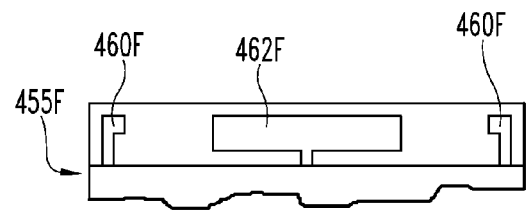
Fig. 30      Fig. 31
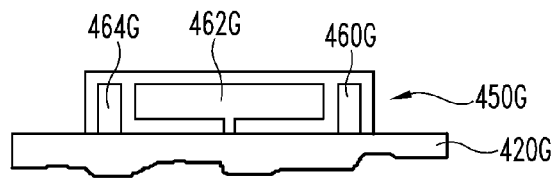
Fig. 32

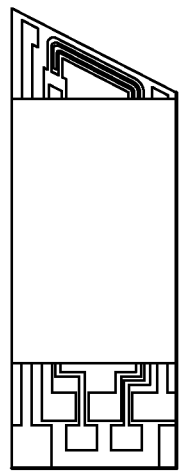 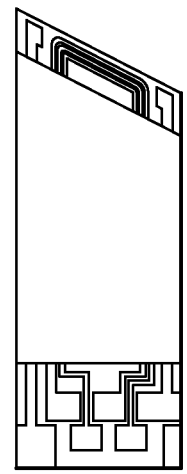
*Fig. 39*  *Fig. 40*

US 8,992,750 B1

BIOSENSOR AND METHODS FOR MANUFACTURING

CROSS-REFERENCE TO RELATED APPLICATION

This application claims the benefit of U.S. Provisional Application No. 61/666,966 filed Jul. 2, 2012, which is hereby incorporated by reference.

BACKGROUND

In many fields of healthcare, repeated measurement and monitoring of certain analytes present in bodily fluids, such as blood or urine, is of particular importance. One special case concerns, for example, patients affected by diabetes who need to measure the concentration of glucose very frequently in order to respond promptly with the correct medication. Exceeding certain blood glucose limits can result in coma or death. Even mildly elevated levels of blood glucose can result in gradually deteriorating health requiring long term monitoring to keep glycemic levels under control. As such, blood glucose data are useful both to the physician who has the task to determine the most appropriate long-term therapy, and to the patient who daily needs to adapt the administration of medications according to the measured glucose levels. These depend not only on the diet, but also on the daily physical activity and many other factors, which influence the metabolism.

A number of small, reliable and low-cost medical devices, which can be handheld, are available today to the patient for self monitoring. Devices for controlled administration of therapeutic agents, such as insulin pumps, are also commercially available. The number of exemplary medical devices to which this invention refers to is, however, not limited to diabetes care. Worth mentioning are, for example, those devices for monitoring blood pressure or other blood parameters like coagulation factors.

Complications associated with the use of such medical devices can arise when the patient or user suffers from poor eyesight or unsteady hands. These conditions might exist, for example, due to a congenital defect, a trauma, or an abnormal concentration of glucose in the blood, especially if the abnormal glucose concentration occurs over long periods. In other words, diabetic patients frequently suffer from visual impairment or a lack of fine motor skills, such as hand tremors.

SUMMARY

A test strip having a sampling end that comprises a "full width end dose" (FWED) structure provides opportunities for improvements in biosensors as well as in their production. As generally contemplated, a FWED test strip can be used in monitoring various disorders, such as diabetes, since it can test fluid samples for the presence or concentration of an analyte, such as blood glucose. The FWED test strip includes a chamber for receiving a liquid sample that spans the width of the test strip at the end where the user places the sample. The sample chamber is open on three sides and sized to allow bodily fluid to enter by capillary action. This arrangement allows the test strip to self vent without the need to specifically manufacture additional vent openings. The sample chamber is bounded on the top and bottom by two substrate layers that are spaced apart by a spacing layer. At least one of the substrates is optionally clear (transparent or translucent) to allow the user to visually confirm dosing of the capillary chamber. Horizontally, the capillary chamber is bounded only by the spacing layer on one side with the remaining periphery of the chamber being open. Described in a different way, top and bottom substrates are cantilevered around a spacing layer to form a sample chamber that is bounded only by the top substrate, the bottom substrate and one end of the spacing layer while being open on all other sides.

Embodiments include a generally square-ended test strip the user is able to dose anywhere along the full front edge of the strip, the front corners of the strip, and even the lateral side edges toward the front edge of the strip. Non-square-ended embodiments, e.g. taper or round ended, provide similar advantageous dosing flexibility. The multiple possible dosing locations provided on the strip can be helpful for those with reduced eyesight, hand dexterity or hand stability difficulties. Embodiments also provide sample chambers that require small volumes of fluid for testing and fill rapidly with sample fluid. Other features include increasing manufacturing efficiencies and cost savings when producing test strips according to other embodiments. Some or all of these features may be present in the corresponding independent or dependent claims, but should not be construed to be a limitation unless expressly recited in a particular claim.

This summary is provided to introduce a selection of the concepts that are described in further detail in the detailed description and drawings contained herein. This summary is not intended to identify any primary or essential features of the claimed subject matter, nor is it intended to be used as an aid in determining the scope of the appended claims. Each embodiment described herein is not intended to address every object described herein, and each embodiment does not include each feature described. Other forms, embodiments, objects, advantages, benefits, features, and aspects of the present invention will become apparent to one of skill in the art from the detailed description and drawings contained herein.

BRIEF DESCRIPTION OF THE DRAWINGS

FIG. 26 is a fragmentary, top plan view of an alternate sampling end electrode pattern according to another embodiment.

FIG. 27 is a fragmentary, top plan view of an alternate sampling end electrode pattern according to still another embodiment.

FIG. 28 is a fragmentary, top plan view of an alternate sampling end electrode pattern according to yet another embodiment.

FIG. 29 is a fragmentary, top plan view of an alternate sampling end electrode pattern according to a further embodiment.

FIG. 30 is a fragmentary, top plan view of an alternate sampling end electrode pattern according to still a further embodiment.

FIG. 31 is a fragmentary, top plan view of an alternate sampling end electrode pattern according to yet a further embodiment.

FIG. 32 is a fragmentary, top plan view of an alternate sampling end electrode pattern according to another further embodiment.

FIG. 39 is a top plan view of a test strip singulated from the sheet of test strips shown in FIG. 41.

FIG. 40 is a top plan view of a test strip singulated from the sheet of test strips shown in FIG. 42.

DETAILED DESCRIPTION OF THE ILLUSTRATED EMBODIMENTS

Figure 1:
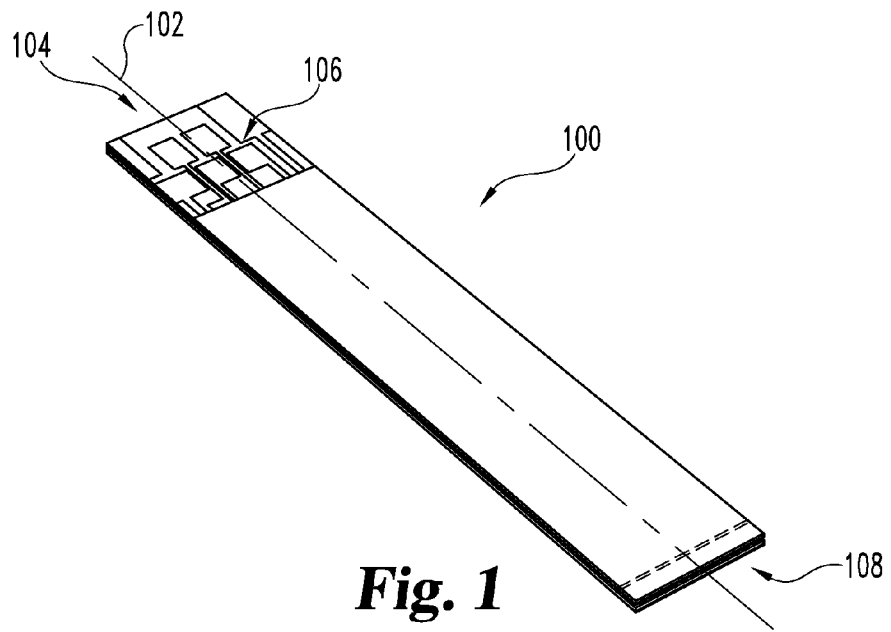
FIG. 1 is a perspective view of a biosensor according to one embodiment.

For the purposes of promoting an understanding of the principles of the invention, reference will now be made to the selected embodiments illustrated in the drawings and specific language will be used to describe the same. It will nevertheless be understood that no limitation of the scope of the invention is hereby intended, such alterations, modifications, and further applications of the principles of the invention being contemplated as would normally occur to one skilled in the art to which the invention relates. At least one embodiment of the invention is shown in great detail, although it will be apparent to those skilled in the relevant art that some features or some combinations of features may not be shown for the sake of clarity.

Depicted in FIG. 1 is a biosensor, for example a test strip 100, according to one embodiment. The test strip 100 is generally shaped as a flat, elongated rectangle defining a longitudinal axis 102. The test strip 100 includes a test meter connection end 104 with an electrode and contact pad pattern 106 that connects with a test meter for determining the concentration and/or presence of an analyte in a sample of bodily fluid. The test strip 100 further includes a fluid sampling end 108, which collects the sample of bodily fluid for testing.

Figure 2:
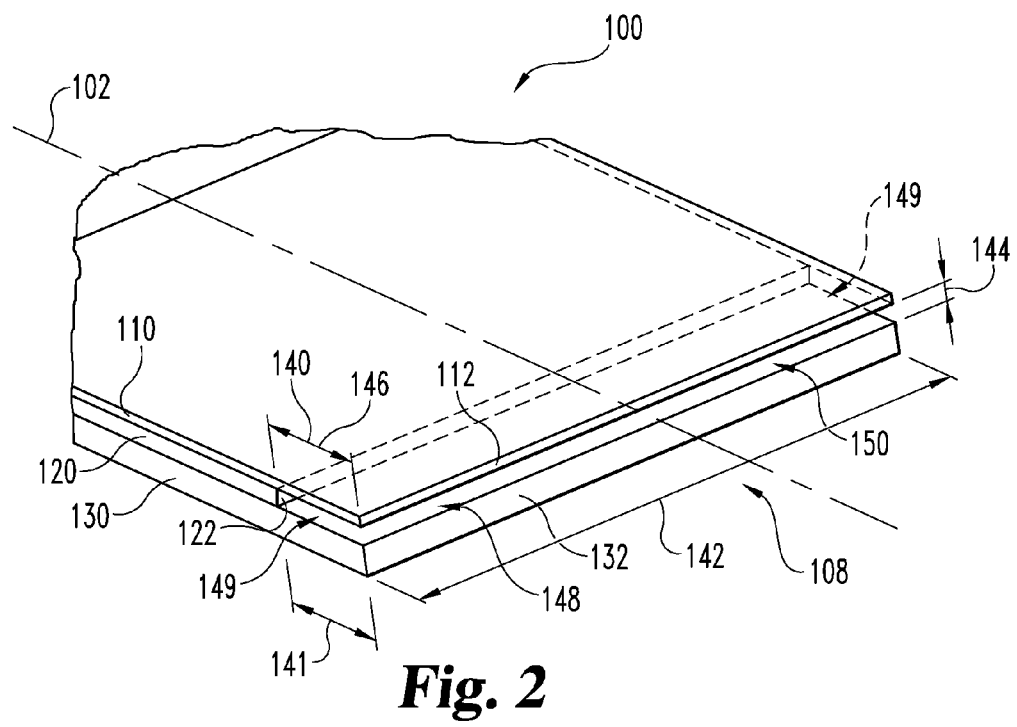
FIG. 2 is a fragmentary perspective view of the fluid sampling end of the biosensor depicted in FIG. 1.

Turning to FIG. 2, the test strip 100 further includes an upper substrate layer 110, a middle substrate layer (for example, a spacer 120), and a lower substrate layer 130. The spacer 120 is positioned vertically between the upper substrate layer 110 and the lower substrate layer 130. A sampling end 108 includes a front edge 112 of the upper substrate layer 110 extending horizontally an overhang distance 140 beyond the front edge 122 of the middle substrate layer 120. Similarly, the front edge 132 of the lower substrate layer 130 extends an overhang distance 141 beyond the front edge 122 of the middle spacer layer 120.

The terms "upper" and "lower" (as well as similar terms such as "top" and "bottom") are used for illustrative purposes in lieu of terminology such as "first" and "second" in an effort to make the description of the illustrated embodiments easier to read and comprehend without narrowing the scope of the embodiments disclosed herein. No directional preference is intended. For example, "first," "second" and "lower" may alternatively be used instead of "upper," and "second," "first" and "upper" (respectively) may alternatively be used instead of "lower." It is understood that the embodiments can be inverted, with the "upper" layer becoming the "bottom" layer and the "bottom" layer becoming the "upper" layer.

The term "front" is also used for illustrative purposes in an effort to make the description of the illustrated embodiments easier to read and comprehend without narrowing the scope of the embodiments disclosed herein. No directional preference is intended. For example, the term "edge" alone may alternatively be used instead of "front edge." It is understood that the embodiments can be rotated, with the "front" becoming the "back."

A sample chamber 150 for receiving a fluid sample for testing is located at the sampling end 108 of the test strip 100. The sample chamber 150 is formed in a space provided between the upper substrate layer 110 and the lower substrate layer 130. A portion of the upper substrate layer 110 forms an upper border of the sample chamber 150, a portion of the lower substrate layer 130 forms a lower border of the sample chamber 150, and the edge 122 of the spacer layer 120 forms a side border of the sample chamber 150. The sample chamber 150 spans the entire width 142 of the test strip 100 and is open on three sides: one front opening 148 and the two side openings 149. The openings 148, 149 are typically contiguous such that the chamber 150 is open all about its periphery without interruption other than by edge 122. This configuration can be referred to as a Full Width End Dose (FWED) configuration. The dimensions of the sample chamber 150 include a height 144, a width 142 and a depth 146. In the illustrated embodiment, the sample chamber depth 146 is generally equal to the upper substrate overhang distance 140, which is typically generally equal to the lower substrate overhang distance 141. In other embodiments, the upper substrate overhang distance 140 can be either longer or shorter than the lower substrate overhang distance 141. An upper substrate overhang distance 140 that is longer than the lower substrate overhang distance 141 may reduce hesitation of sample uptake into the sample chamber 150. It also allows for a more angled approach of a test strip 100 to a targeted sample mass. A further description of producing such disparate overhang distances such as this is provided herein below.

Figure 3:
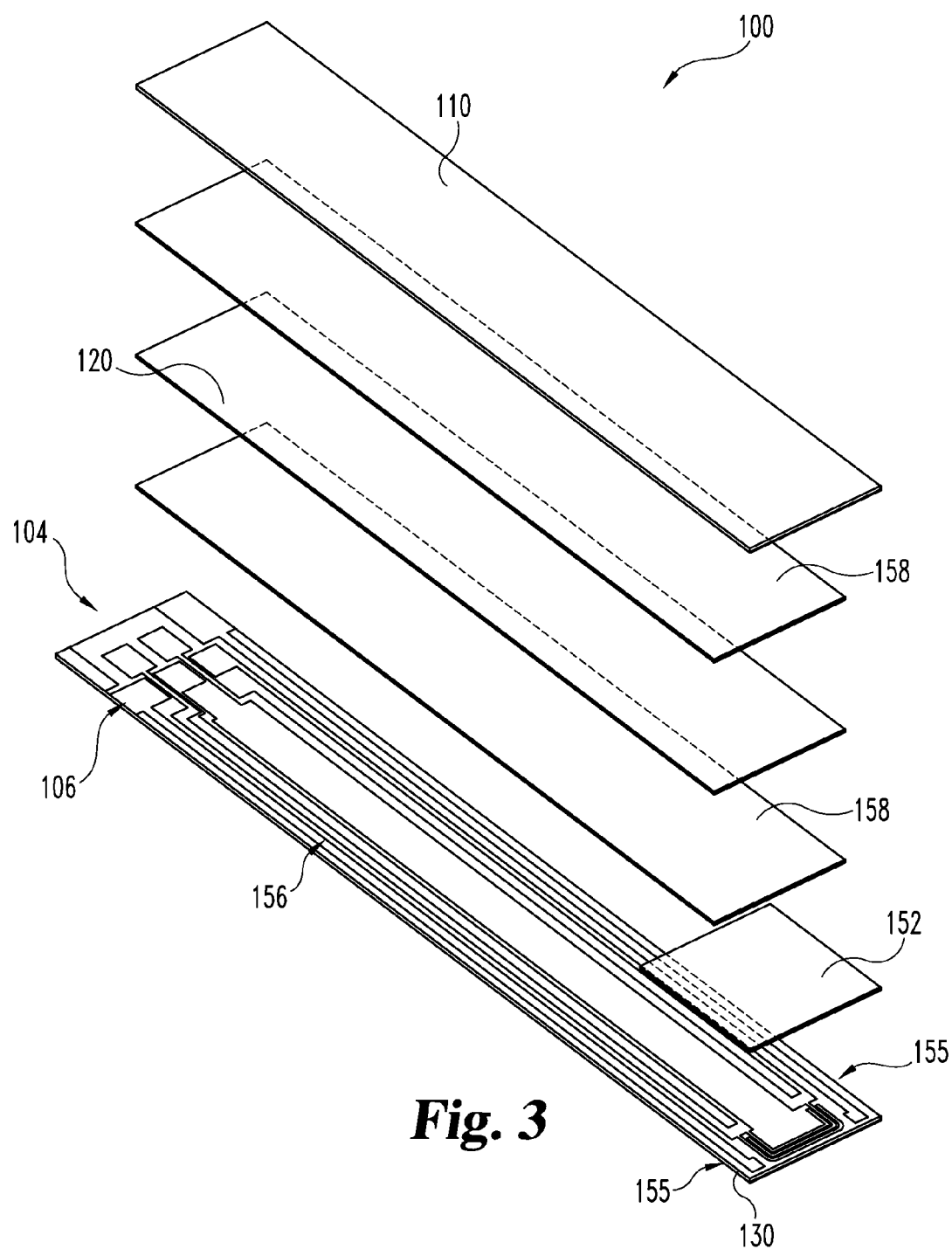
FIG. 3 is an exploded perspective view of the biosensor depicted in FIG. 1.

Referring to FIG. 3, the test strip 100 further includes a reagent, for example the reagent layer 152, which reacts with the fluid sample during testing. In the illustrated embodiment, the reagent layer 152 overlies and contacts an electrode pattern 155 that is formed at the sampling end 108. The electrode pattern 155 is formed in the sample chamber 150 and generally contacts the sample fluid directly during testing. The electrode pattern 155 is electrically connected to the contact pad pattern 106 at the test meter connection end 104 of the test strip 100 by the electrode traces 156. An adhesion layer 158 is positioned between the lower substrate layer 130 and the spacer 120, and binds the lower substrate layer 130 and the spacer 120 together. A second adhesion layer 158 is positioned between and binds the upper substrate layer 110 and the spacer 120 together. Together the spacer 120 and first and second adhesion layers 158 have a combined thickness sufficient to define the desired height 144 of the sample chamber 150. In one alternative embodiment, spacer 120 comprises a two-sided adhesive layer, such as a pressure-sensitive adhesive (or PSA), such that separate adhesion layers 158 are not required. In such embodiments, the two-sided adhesive layer, such as a double sided tape, has a thickness sufficient to define the desired height 144 of the sample chamber 150.

Examples of adhesives that can be employed in many embodiments include pressure-sensitive adhesives, hot melt and other heat sealable adhesives, and cold sealable adhesives. In yet other embodiments, rather than using adhesion films or layers, the layers of the biosensor can be fixed together by heat or laser sealing according to such methods as are generally known in the art.

Figure 4:
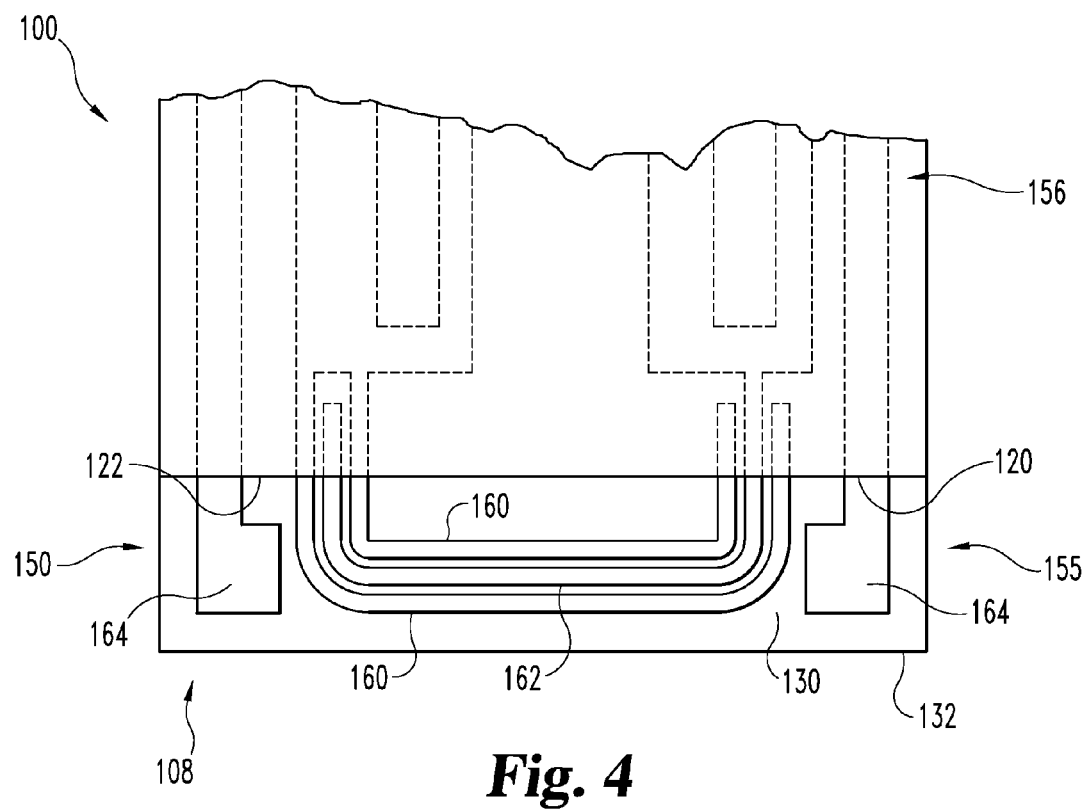
FIG. 4 is a fragmentary, top plan view of the fluid sampling end of the biosensor depicted in FIG. 1.

Depicted in FIG. 4 is an enlarged view of one embodiment of an electrode pattern 155. The illustrated electrode pattern 155 includes two branches of a counter electrode 160 in a generally U-shaped pattern with a working electrode 162 positioned between the two branches of the counter electrode 160. The gap or spacing between the counter electrode 160 and working electrode 162 is maintained at a substantially equal distance, as desired for the functionality of the biosensor, along the lengths thereof exposed within the chamber 150. In other embodiments, only a singular (i.e. non-branched) counter electrode 160 can be provided in the sample chamber 150. The smooth U-shaped transition as shown in FIG. 4 can be beneficial when testing with an alternating electrical current and can be produced using, for example, broad field laser ablation techniques or other high-definition, high precision quality methods of forming electrode patterns, such can be achieved with the current state of the art in ink jetting techniques.

In one embodiment, broad field laser ablation is used in a reel to reel configuration to form multiple electrode patterns 155 with each laser pulse. That is, two or more adjacent patterns can be formed by a single laser pulse as a web of metalized substrate is wound through a laser ablation chamber. By forming multiple patterns with a single pulse, the throughput of the electrode forming step in the overall manufacturing process is increased. This can typically be achieved using known broad field laser ablation technology by providing an appropriate laser mask that includes the multiple electrode patterns (and thus is larger than a single-pattern mask), and a lens for directing the laser through the mask, which lens provides a broader dispersion of the laser to be sufficiently directed through the larger mask. This multiple pattern formation using a single pulse also provides advantages in the 2-up manufacturing process discussed further below.

As shown in the illustrated embodiment, two sample sufficiency electrodes 164 are spaced laterally outside the counter 160 and the working 162 electrodes. The location of the sufficiency electrodes 164 on each lateral side of the sample chamber 150 helps to ensure that testing does not begin (once the test strip is inserted into a meter) until the sample fluid fully covers the working electrode. That is, the sample fluid must bridge the gap between the sample sufficiency electrodes before analysis is allowed to begin, using known methods for electrically detecting such bridging by a fluid.

Figure 5:
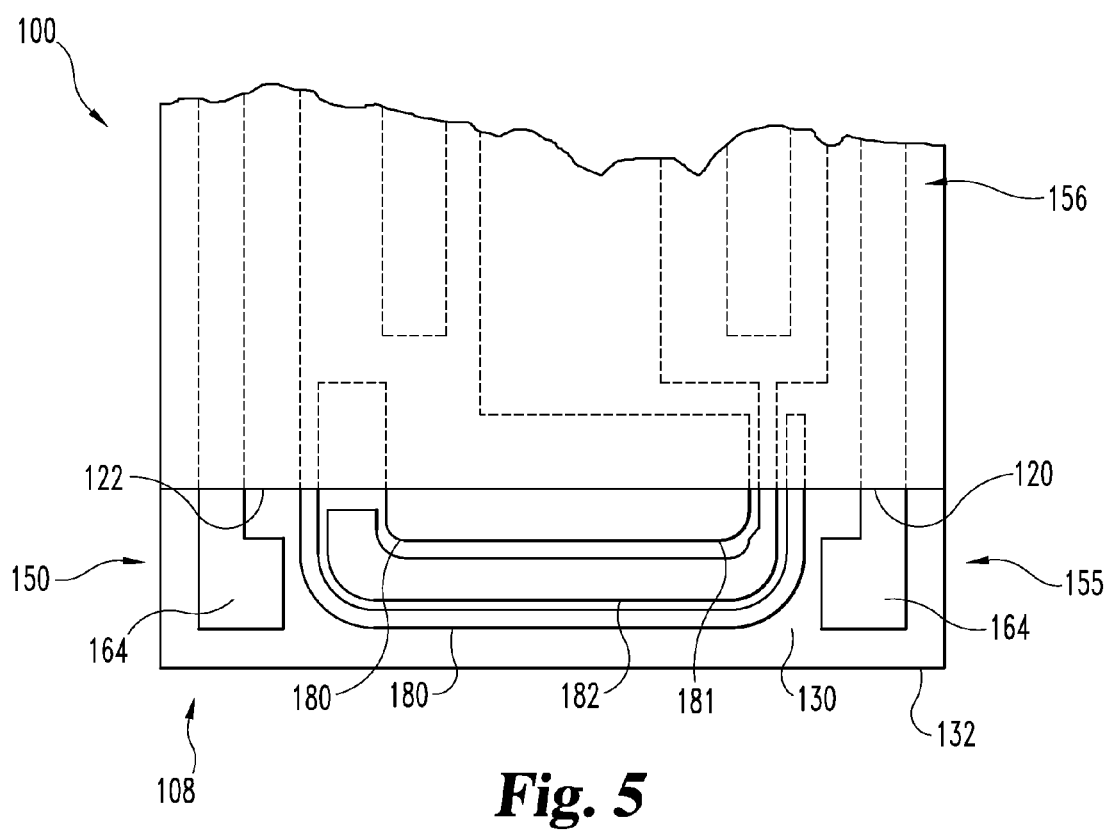
FIG. 5 is a fragmentary top plan view of the fluid sampling end of a biosensor showing an alternative embodiment of an electrode pattern configuration in the sample chamber.

An alternative embodiment of an electrode structure is shown in FIG. 5, in which the working electrode 182 terminates in the chamber and the counter electrode 180 includes an enlarged counter electrode block portion 181 rather than a second branch as with counter electrode 160. The working electrode 182 is also necked-down as it extends from the chamber to under the spacer layer 120 so that, in combination with the working electrode terminating within the sample chamber 150, there is a mitigated, lessened variation of the effective (exposed) working electrode area in the sample chamber depending on location of the edge 122, thereby minimizing variation in the measured current response, which depends directly on effective area of the working electrode.

Figure 6:
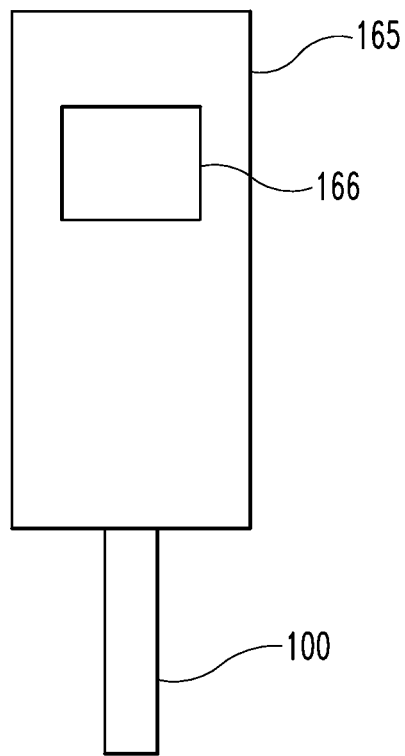
FIG. 6 is a plan view of the biosensor depicted in FIG. 1 inserted into a test meter.

In use, a test meter connection end 104 is inserted into a test meter 165 as depicted in FIG. 6. The test meter 165 includes a display 166 for providing information and/or directions to a user. A sample fluid is obtained, for example a blood or interstitial fluid sample obtained typically by penetrating the skin surface with a sharp object such as a lancet or a needle. As the sample fluid emerges from the wound, it collects on the surface of the skin and the user brings the droplet of sample fluid in contact with an opening to the sample chamber 150. Typically, the fluid is placed in contact with the front opening 148 (along the width 142 of the sample chamber), although the fluid may also be placed in contact with a side opening 149 (along the depth 146 of the sample chamber 150) or with a corner opening joining a side opening and front opening. When the fluid contacts an opening to sample chamber 150 (e.g., the front opening 148 or the side opening 149), the sample chamber 150 draws the fluid inward by capillary action. When being drawn inward from the front opening 148, the fluid typically comes into contact with the front edge 122 of the spacer 120 and begins spreading laterally in various directions.

Figure 7:
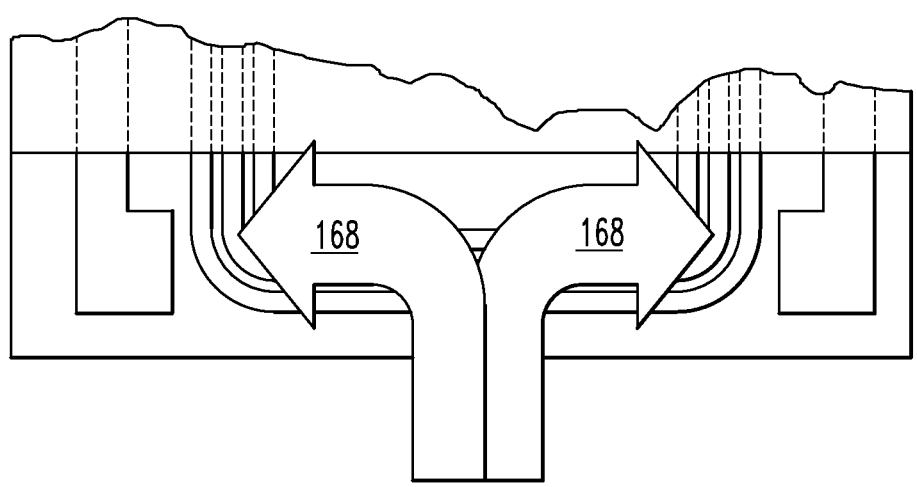
FIG. 7 is a fragmentary, top plan view of the fluid sampling end of the biosensor depicted in FIG. 1 with a directional illustration of fluid entering the sample chamber.

FIG. 7 depicts the general manner in which a sample of fluid entering the sample chamber at opening 148 spreads as the sample fills the sample chamber 150. In the depicted example, the sample fluid enters at the approximate center of the sample chamber width and spreads in a generally T-shaped nature, moving generally inward and then generally outward along the directions 168. As the sample fills the depths of sample chamber 150, the sample flows in a direction that is generally perpendicular to the longitudinal axis 102 of test strip 100. By simultaneously filling in two directions, the sample chamber 150 can fill quicker than similarly sized sample chambers that fill in only one direction.

Figure 8A:
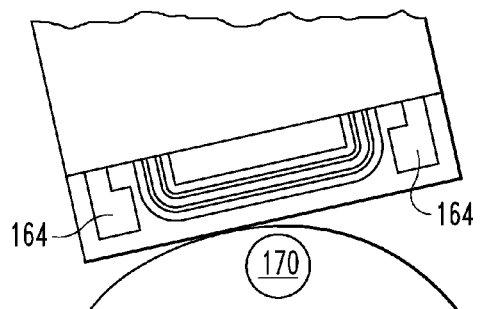
FIGS. 8A, 8B, 8C, 8D, 8E and 8F are fragmentary, top plan views of the biosensor depicted in FIG. 1 sequentially illustrating a fluid sample entering the sample chamber.
Figure 8B:
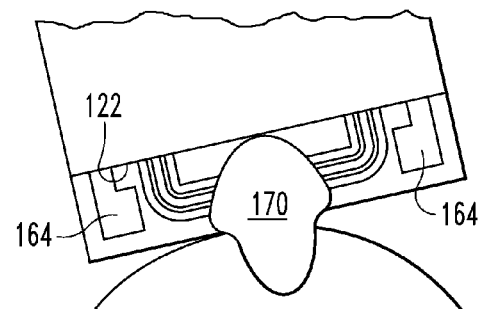
Figure 8C:
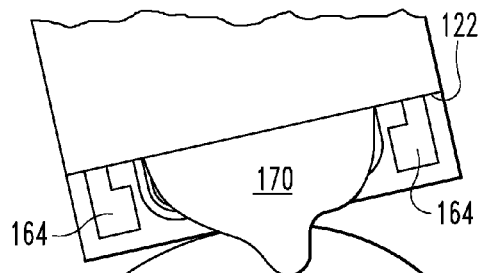
Figure 8D:
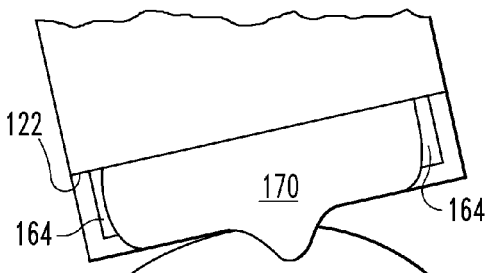
Figure 8E:
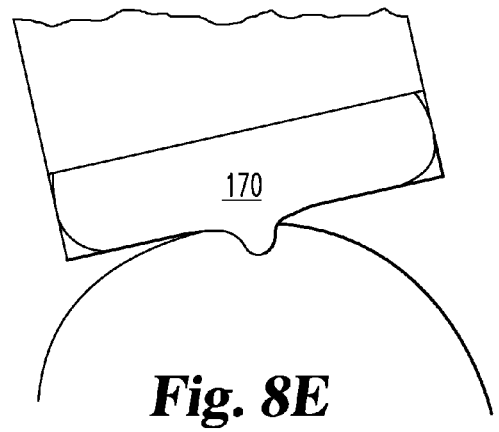
Figure 8F:
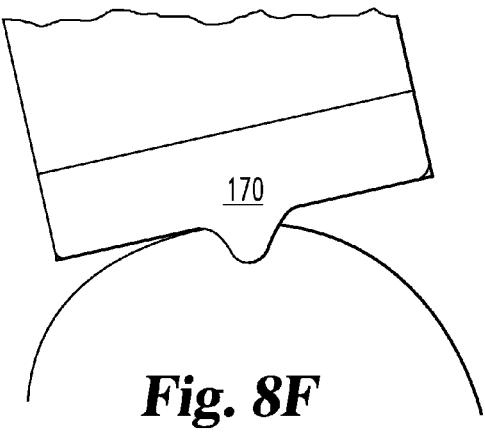

FIGS. 8A-8F also depict, although in an alternative presentation, the manner in which a fluid sample fills the sample chamber 150 in two-dimensions. FIG. 8A depicts the droplet of sample fluid prior to contact with the sample chamber 150. FIG. 8B depicts the droplet of sample fluid 170 spreading inward into the sample chamber 150 and at the point the droplet of sample fluid 170 begins contacting the front edge 122 of the spacer 120. FIG. 8C depicts the droplet 170 spreading outwardly in two directions and along the front edge 122 of the spacer layer 120. FIG. 8D depicts the droplet 170 contacting the sample sufficiency electrodes 164. FIGS. 8E and 8F depict the droplet 170 continuing to fill the sample chamber 150.

The arrangement of the sample chamber 150 with three open sides further allows the sample chamber 150 to "self vent" along the open portions of the perimeter of the sample chamber as the sample chamber fills with fluid. This ability to vent along a substantial amount of the sample chamber perimeter further provides the ability for the sample chamber 150 to fill rapidly with fluid.

Moreover, a sample chamber having a substantially open perimeter, e.g. along the three sides in test strip 100 as illustrated, presents fewer impediments to the fluid filling the capillary chamber, thereby enhancing the sample chamber's ability to fill rapidly with fluid. For example, fluid entering a prior art sample capillary channel can adhere to the side walls of the channel and slow the rate at which the channel fills. Furthermore, adhesives that hold layers of the test strip together are typically hydrophobic and can further reduce fill times. Typical capillary channels are formed with two or three side walls, which slows the rate at which the sample chamber defined by the channel fills. However, in embodiments of the present invention, the sample chamber 150 has only one side wall (the side wall including forward edge 122 of spacer layer 120) for fluid to adhere to, which allows the fluid to fill chamber 150 more quickly than if chamber 150 had either two or three side walls. Of course, as will be appreciated by those of ordinary skill in the art, the top and bottom surfaces of a channel or chamber are easier to make hydrophilic, by either a special coating or by appropriate formulation of the reagent layer that covers most or all of the bottom of the channel or chamber, to exhibit enhanced hydrophilic properties. But the affect of these can be hindered by the difficulties described above relating to the side walls of a channel. By reducing the number or extent of exposed side walls, a FWED test strip enjoys faster fill times, as detailed further below.

Embodiments of the present invention exhibit improved sample acquisition characteristics. For example, unexpectedly fast fill times were realized when testing embodiments of the disclosed invention. Fast fill times reduce the amount of time required by users to test sample fluid. Fast fill times also result in less evaporation, which, for example, reduces the total amount of blood that must be expressed from a user. Smaller sample sizes enable the user to obtain blood from alternate test sites that may not be as vascular but do not result in as much pain. In some embodiments, the lower surface of the upper substrate layer 110 (the surface facing the sample chamber 150) is comprised of hydrophilic material, which can further enhance the ability of the sample chamber 150 to rapidly fill with fluid. In other embodiments, the bottom of the sample chamber 150 is coated with a reagent layer 152 that is hydrophilic, which can also enhance the ability of the sample chamber to rapidly fill with fluid. In one embodiment, beginning from the time the sample first contacts the front opening, a side opening or corner opening, and ending when the sample sufficiency electrodes (in the presence of an applied potential from a connected meter) detect fluid sample bridging therebetween, the sample chamber 150 fills in at most 0.3 seconds, while in another embodiment the sample chamber 150 fills in at most 0.1 seconds. And in still further embodiments, when a sample is dosed by contacting the front edge opening, the sample chamber 150 fills in at most one-thirtieth (1/30) of a second (approximately 0.033 seconds).

The arrangement of the sample sufficiency electrodes 164 on opposing sides of the sample chamber may be used to ensure that the sample chamber is adequately filled with fluid prior to the initiation of testing. If sample fluid is introduced off center, such as along one of the side openings 149 or near the corner of the sample chamber 150 between the side opening 149 and the front opening 148, the arrangement of the sample sufficiency electrodes 164 bracketing the working electrode 162, and possibly also the counter electrode 160, can serve to inhibit testing until the working electrode 162 and/or the counter electrode 160 is fully covered by the sample to provide accurate testing. As such, the sample chamber 150 may be considered to be full, at least for testing purposes, before the fluid reaches all edges of the sample chamber 150.

In one embodiment, at least the upper substrate layer 110 is transparent in the region of the sample chamber 150 to provide visual feedback to the user while the sample chamber 150 fills with fluid. Once the user verifies that the sample chamber 150 is filled with fluid, either by visual confirmation through a transparent upper substrate layer 110 or by the test meter providing an indication when the sample sufficiency electrodes 164 are covered with fluid, the user can remove the supply of sample fluid from the sample chamber to avoid perturbing the fluid in the sample chamber 150 during testing, which could adversely affect the test results.

It was discovered that the aspect ratio of the sample chamber 150 (the ratio equal to the sample chamber depth 146 divided by the sample chamber width 142) affected the fill times of the sample chamber 150. In general, smaller aspect ratios result in quicker fill times than larger aspect ratios. Sample chambers with aspect ratios less than 1.0 were capable of two-dimensional filling (see, e.g., FIGS. 7-8F), which decreased the total time required to fill the sample chamber. To achieve two-dimensional filling with the sample fluid contacting the front edge 122 of the spacer layer 120 prior to spreading out sideways along the width of the sample chamber 150, it is desirable to have the sample chamber depth 146 less than the sample chamber width 142. Stated differently, aspect ratios of less than 1.0 provide for rapid fill times of the sample chamber 150. Aspect ratios greater than 1.0 can result in incomplete filling of the sample chamber 150 and can potentially result in air being trapped over the working electrode 162 and/or the counter electrodes 160 resulting in testing errors. In one embodiment, the sample chamber 150 has an aspect ratio of 0.2 with, for example, the sample chamber depth 146 being one millimeter (1 mm) and the sample chamber width 145 being five millimeters (5 mm). In other embodiments, the aspect ratio of the sample chamber 150 is at least one-ninth (⅑, approximately 0.1) and at most one-third (⅓, approximately 0.3). In an alternate embodiment, the aspect ratio is at least one-sixth (⅙, approximately 0.17) and at most one-quarter (¼, or 0.25).

In addition to the aspect ratio, the overall dimension (size) of the sample chamber affects how quickly the sample chamber fills. In general, less fluid is required to fill a small sample chamber than a large sample chamber, indicating that the time to fill a small sample chamber should be less than a larger sample chamber. However, it was discovered that certain smaller dimensions for sample chamber height 144 would result in increased fill times. For example, when sampling whole blood, the fill times for the sample chamber 150 increases as the sample chamber height 144 decreases below one hundred micrometers (100 µm). As depicted in Table 1, as the height 144 of the sample chamber 150 decreased from about one hundred fifty-two micrometers (152 µm) to about eighty micrometers (80 µm), the time to fill the sample chamber 150 increased from about 0.28 seconds to about 0.42 seconds.

TABLE 1

SAMPLE CHAMBER FILL TIMES

| Average Capillary Height (µm) (Actual capillary heights varied from 78 to 158 µm, using four basic spacer thicknesses) | Average Fill Time at Room Temperature (msec) |
| --- | --- |
| 151.7 | 280.0 |
| 124.8 | 317.6 |
| 94.2 | 356.8 |
| 79.3 | 415.2 |

The data in Table 1 was obtained using nominal hematocrit blood surrogate on 7 mm wide strips dosed from the front edge of a FWED strip. It is expected that the fill times for the sample chamber 150 will be higher when dosing with sample fluid having higher than nominal hematocrit levels, e.g. 65-85%. Sample chambers adapted to sample and test serum, plasma, or aqueous solutions can use a smaller sample chamber height and can potentially achieve faster fill times.

In one embodiment, the height 144 of the sample chamber 150 is at least seventy micrometers (70 µm) and at most two hundred micrometers (200 µm). In an alternate embodiment, the height 144 of the sample chamber 150 is at least one hundred micrometers (100 µm) and at most one hundred fifty micrometers (150 µm). In still another embodiment, the height 144 of the sample chamber 150 is one hundred thirty micrometers (130 µm). When sampling and testing whole blood, a minimum capillary height of one hundred micrometers (100 µm) is frequently used to provide rapid fill rates even with a seventy percent (70%) hematocrit blood sample.

Although FIGS. 7-8F depict a droplet of sample fluid being applied to the center of the sample chamber, it should be appreciated that the droplet may be applied anywhere along the width of the test strip 100—anywhere along the front opening 148. The ability to place the sample anywhere along the full width of the test strip 100 is advantageous for all users, especially those with diminished eyesight, which is not uncommon with diabetics, since someone with diminished eyesight may not be able to place the sample at an exact location along the width of the test strip. Additionally, users who are unable to hold their hands steady while applying the sample, which is also not uncommon with diabetics, will receive benefit since the sample may be applied anywhere along the edge of the test strip. As such, advantages are realized if the width 142 of the test strip 100 is sufficiently large to allow impaired users to easily use the test strip 100. In one embodiment, the width 142 of the sample chamber 150 is at least three millimeters (3 mm) and at most nine millimeters (9 mm). In another embodiment, the width 142 of the sample chamber 150 is at least four millimeters (4 mm) and at most six millimeters (6 mm). In still another embodiment, the width 142 of the sample chamber 150 is five millimeters (5 mm).

While the ability of the sample chamber 150 to fill two-dimensionally enhances the ability of the sample chamber 150 to fill rapidly, the relatively small size of the sample chamber 150 further enhances its ability to fill rapidly and minimizes the amount of sample fluid required for testing. For example, the more fluid required for testing, the more time will be required to fill the sample chamber given the same or similar flow rate of fluid into the sample chamber. However, too small of a sample volume can, through evaporation, result in relatively large sample size variations during testing, which can adversely impact test results. In balancing these and other factors, alternate embodiments include sample chamber volumes that are at most one thousand nanoliters (1,000 nl), five hundred nanoliters (500 nl), and one hundred nanoliters (100 nl).

For a given sample chamber width 142, a larger sample chamber depth 146 increases the volume, increases the aspect ratio and increases sample chamber fill times of the sample chamber 150. However, the sample chamber depths 146 that are too small can have adverse effects during the manufacturing process. For example, when producing test strips using the methods described in relation to, for example, FIG. 13 below, small errors in separating the head-to-head oriented test strips will result in large variations in sample chamber volume when the sample chamber depth is small. Embodiments include the sample chamber depths 146 equal to at most one and one-half millimeters (1.5 mm). Alternate embodiments include the sample chamber depths 146 equal to at most one millimeter (1.0 mm).

The electrode pattern 155 is typically formed on one substrate layer—the lower substrate layer 130. However, alternate embodiments include opposing (otherwise referred to as "facing") sample end electrode patterns that are formed on two substrate surfaces that face one another in the assembled test strip. This arrangement can assist in further reducing test strip width. However, if a test strip is too narrow it can be difficult for users to handle, especially impaired users.

Forming the electrode pattern on a single substrate can help reduce variations in electrode separation, which can adversely affect test strip performance and test results. The separation distance between facing electrodes (electrodes that are formed on two facing substrate layers and face one another) changes with variations in sample chamber height, such as variations in sample chamber height caused by varying the thickness of spacer 120 or adhesion layer 158. However, variations in sample chamber height do not affect the separation between electrodes formed on the same substrate. This feature can be particularly beneficial when producing test strips intended for use without entry of a batch-related code (generally related to a correction factor) prior to use. Further advantages of coplanar electrodes (electrodes located on the same plane, such as when they are formed on the same substrate layer) can be realized during manufacture since one or more simple changes can be made to the electrode pattern design to adjust the geometry, size or spacing of electrodes as needed or desired.

Furthermore, in other embodiments, including the electrode pattern 155 on a single substrate (e.g., the lower substrate layer 130) allows the other substrate layer (e.g., the upper substrate layer 110) to be transparent or translucent, which assists the user to clearly identify the sample location and obtain visual confirmation that the sample chamber is properly filling and/or filled. The ability to obtain visual feedback of the sample chamber filling with fluid provides advantages in helping the user know to stop trying to fill a full sample chamber, since attempting to fill an already full sample chamber can perturb the sample and adversely affect the test results.

In other embodiments, translucent layer 110 may be used as a light guide or light pipe to carry illumination from a light source, e.g. from a strip port on a meter, placed adjacently to the contact end of the biosensor to the other end of the strip. The illumination allows a user to visualize the dose area 148 of the strip in low light conditions. The light is emitted along edge 112 and can provide illumination to visualize a sample to be applied.

Further advantages of a transparent or translucent upper substrate layer, also referred to commonly as a cover, lid, or roof by those of ordinary skill in the art, are set forth in U.S. Pat. No. 5,997,817 to Crismore, the disclosure of which is incorporated herein by reference.

Referring to FIG. 2, the lower substrate overhang distance 141 generally equals the upper substrate overhang distance 140, which generally aligns the upper substrate front edge 112 and the lower substrate front edge 132. Manufacturing efficiencies can be realized by aligning the edges 112 and 132 in this way, especially when using a 2-up manufacturing process as described with respect to, for example, FIG. 13 below, since a single vertical cut can be made through both the upper substrate layer 110 and the lower substrate layer 130 when test strips are separated from one another during the singulation process. Alternate embodiments can, however, include upper and lower substrate layers that extend different overhang distances beyond the spacer layer provided that the biosensor is able to effectively collect and test a sample fluid.

The characteristics discussed above combine to enhance the user's ability to test right the first time, instead of having to repeat the test to obtain accurate results.

Figure 9:
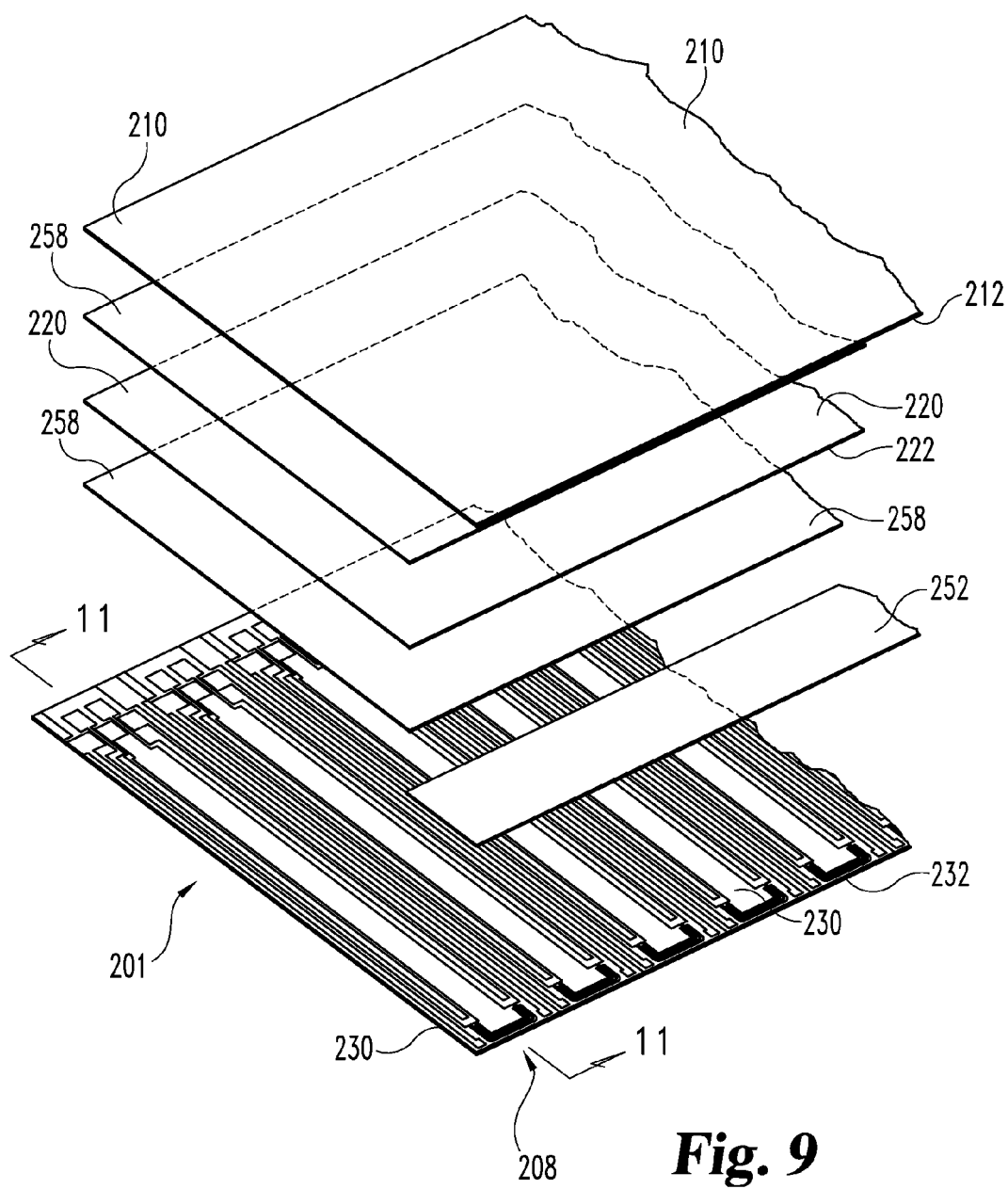
FIG. 9 is an exploded, fragmentary view of a plurality of biosensors prior to lamination during manufacture according to another embodiment.
Figure 10:
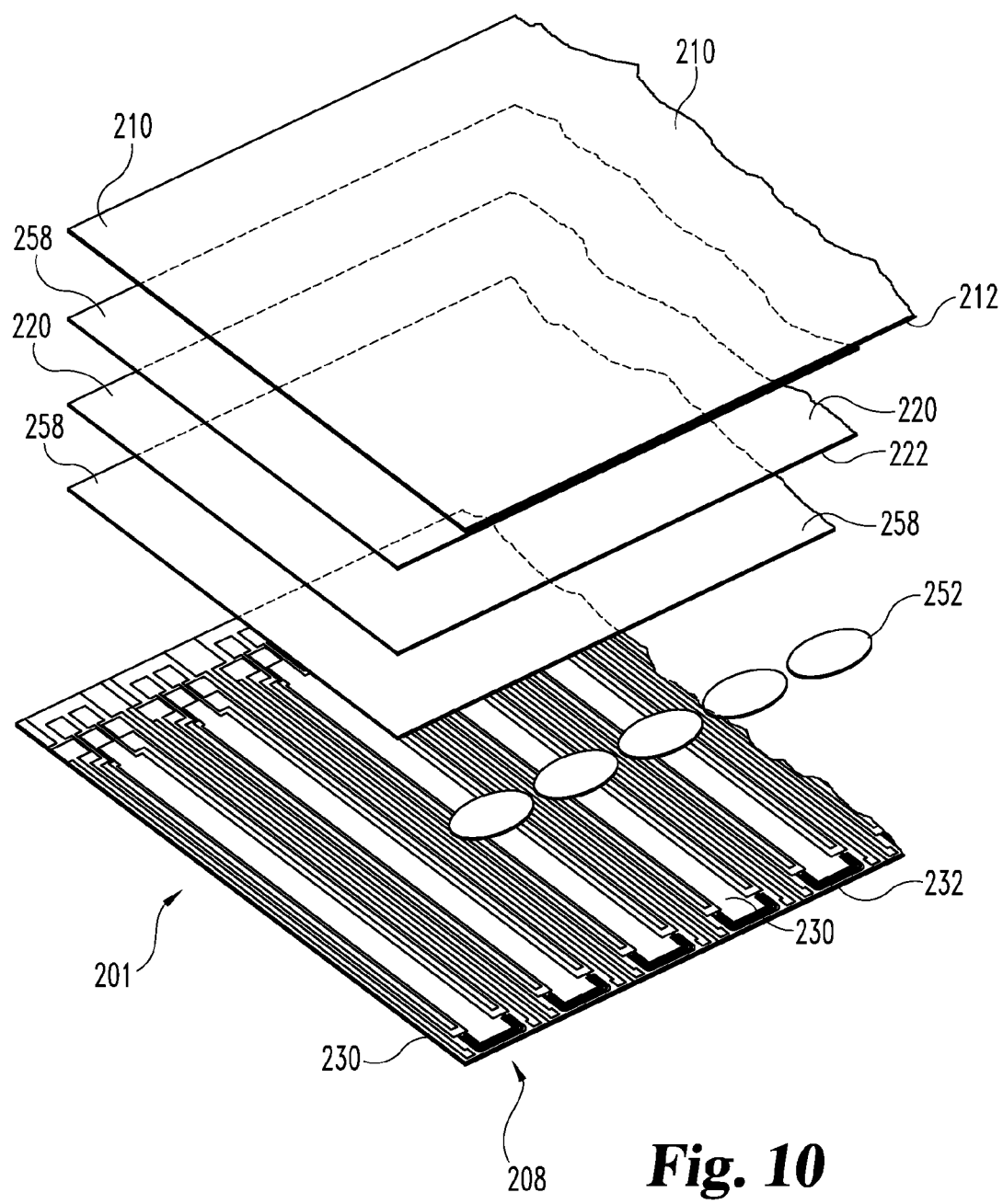
FIG. 10 is an exploded, fragmentary view of a plurality of biosensors prior to lamination during manufacture according to yet another embodiment employing a discrete reagent layer deposition method.

The test strips as described herein provide additional advantages during the manufacturing process. For example, a plurality of side-by-side oriented electrode patterns 201 can be formed on an elongated supply roll (tape) of the lower substrate 230 using, for example, a high speed reel-to-reel manufacturing process (also referred to as roll-to-roll, R2R, and web processing) as depicted in FIG. 9. A reagent layer 252, in the form of a continuous stripe in the illustrated embodiment, is applied to the sampling end 208 of the elongated supply of the lower substrate 230. The reagent layer 252 may be applied using a high speed coating process such as a modified slot die coater with vacuum assist, or may be applied using, for example, blade coating, dispensing, inkjet coating, screen printing and rotary screen printing. An exemplary embodiment having more discrete deposition of the reagent layer 252 is illustrated in FIG. 10.

For a continuous stripe deposition of the reagent layer 252, it is possible for the reagent layer 252 to extend beyond the edge 232 of the lower substrate layer 230 during manufacture without adversely affecting the operation of the finished test strips. The excess reagent applied beyond the edge 232 of the lower substrate layer 230 is simply not included in the sample chamber. The relaxed tolerances for application of the reagent layer 252 will decrease the need to shut down or otherwise tightly control the assembly line due to reagent layer positioning inaccuracies, result in a lower percentage of test strips being unusable due to misalignment of the reagent layer 252, enable a faster running assembly process, and generally help increase manufacturing efficiencies.

Reagent waste is also reduced by not having lateral sides to the sample chamber. For example, if the sample chamber were not open on the lateral sides (e.g., if the sample chamber 150 in FIG. 2 did not have the side openings 149), but was instead bordered by the spacer layer 220, the layer of reagent 252 would be applied in regions covered by the spacer layer 220 and not in the sample chamber.

The disclosed manufacturing process eliminates the registration and alignment steps that are required during manufacturing of other biosensor test strips, creating a more efficient, streamlined and cost effective manufacturing process. For example, there is no need to form holes in any of the layers to create an air vent, or align the vent with a sample chamber. The vent structure is automatically formed with the forming of the sample chamber by using edge guided web steering during the multi-layer lamination process. No additional materials or secondary die cutting or laser cutting is required to create the capillary and venting structures.

An elongated layer (tape) of middle substrate is placed on top of and attached to the lower substrate layer 230 to form a spacer layer 220. Edge guiding techniques can be used to ensure that the edge 222 of the spacer layer 220 is positioned an appropriate controlled distance from the edge 232 of the lower substrate layer 230 to create the proper sample chamber depth. Alternatively or in addition, the front edge 222 of spacer layer 220 can be positioned with regard to the location of the electrode pattern, e.g. 155, to control the area of the electrodes, exposed within the sample chamber 250. In the illustrated embodiment an adhesion layer, for example adhesive layer 258, is positioned between the lower substrate layer 230 and the spacer layer 220. Adhesive layers 258 may be applied to the spacer layer 220 before cutting the material to the finished width. This operation allows adhesive, e.g., to be applied to the edge of the spacer layer 220 to allow sealing the edge precisely without worrying about placement of the adhesive layer 258.

An elongated layer (tape) of upper substrate 210 is positioned over and attached to the spacer layer 220. The edge 212 of the upper substrate layer 210 is aligned with the edge 232 of the lower substrate layer 230, typically using edge guiding techniques. Alternatively or additionally, a cutting device may be used after the upper substrate layer 210 is attached to the spacer layer 220 to ensure that the edge 212 of the upper substrate layer 210 is positioned the proper distance from the edge 222 of the spacer layer 220. In the illustrated embodiment, the overhang distance that the upper substrate layer 210 extends past the spacer layer 220 is generally equal to the overhang distance that the lower substrate layer 230 extends past the spacer layer 220, resulting in the vertical alignment between the edge 212 of the upper substrate layer 210 and the edge 232 of the lower substrate layer 230. In alternate embodiments, the edge 212 of the upper substrate layer 210 does not vertically align with the edge 232 of the lower substrate layer 230 provided that the ability of the sample chamber to draw fluid and fill is preserved. In the depicted embodiment, the upper substrate layer 210 is bonded to the spacer layer 220 with an elongated layer (tape) of the adhesive layer 258.

Figure 11:
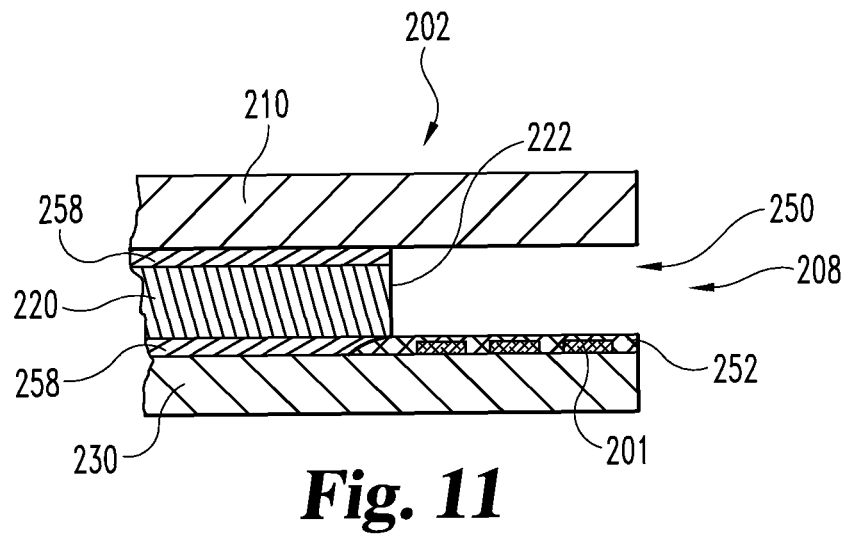
FIG. 11 is a fragmentary, sectional view of the test strip depicted in FIG. 9 after lamination.

Depicted in FIG. 11 is a cross-sectional view of the sampling end 208 of an example test strip 202 after the layers have been attached to one another. In particular, FIG. 11 depicts upper substrate layer 210 attached to adhesive layer 258, which is attached to the spacer layer 220, which is attached to another adhesive layer 258, which is attached to the lower substrate 230. Formed between the upper substrate 210 and the lower substrate 230 and adjacent the spacer layer 220 and the adhesive layers 258 is the sample chamber 250. Located within sample chamber 250 and above lower substrate 230 are electrode pattern 201 and reagent layer 252. As depicted, reagent layer 252 extends slightly under the adhesive layer 258 that attaches the spacer 220 to the lower substrate layer 230. However, this is not required, in the event the reagent layer can be discretely deposited relative to the front edge 222, as may be desired.

Figure 12:
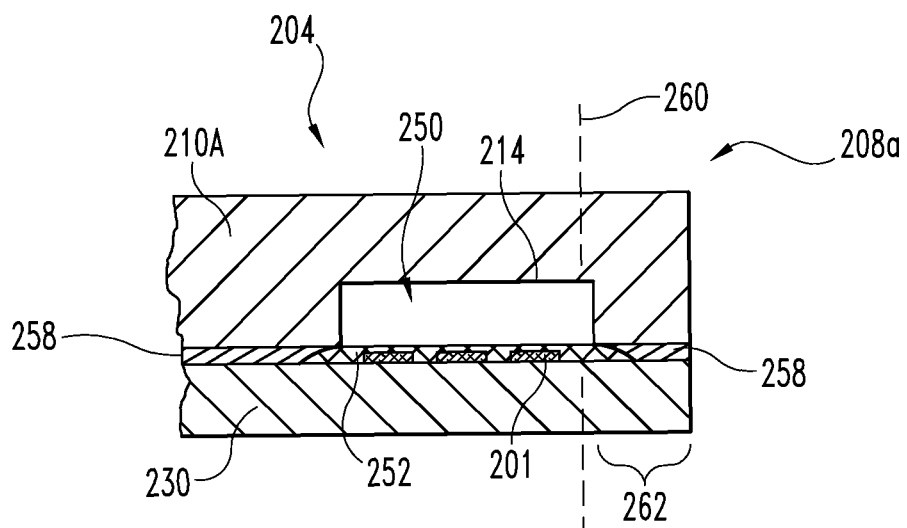
FIG. 12 is a fragmentary, sectional view of a test strip according to still another embodiment.

Depicted in FIG. 12 is the sampling end 208A of a test strip 204 according to another embodiment of the present invention. The location of the cross-sectioning of test strip 204 in FIG. 12 is similar to the location of the cross-sectioning of test strip 202 in FIG. 11. Test strip 204 includes an upper substrate layer 210A, a lower substrate layer 230, and an adhesive layer 258. The upper substrate layer 210A includes a recess, for example groove 214, which forms sample chamber 250 when upper substrate 210 is attached to lower substrate 230. Located in the sample chamber 250 and adjacent to the lower substrate 230 are electrode pattern 201 and reagent layer 252. To expose test chamber 250, the upper substrate 210A and the lower substrate 230 are cut along line 260. Line 260 as shown is located just within the groove 214, which prevents cutting through any adhesive layer which would be more difficult, and provides a degree of useful tolerance for the actual cutting or slitting. In other embodiments, the cut line 260 may be located at the end of groove 214 as desired. Cutting of the upper substrate 210A and the lower substrate 230 is accomplished during the manufacture of test strip 204. In alternate embodiments, the upper substrate 210A and the lower substrate 230 are perforated along line 260 to allow removal of the end portion 262 either during the manufacturing process or by the user of test strip 204.

In one embodiment, groove 214 is formed by laser ablation. In alternate embodiments, groove 214 is formed using a calendering process, which provides the finished test strips with a flat profile and promotes efficient stacking of the test strips for packaging or shipping. In still further embodiments, groove 214 is formed by skiving or by embossing. An upper substrate 210A with groove 214 defines the upper boundary of chamber 250 without the need of using a spacing layer; and thus certain manufacturing and cost efficiency opportunities are provided.

Figure 13:
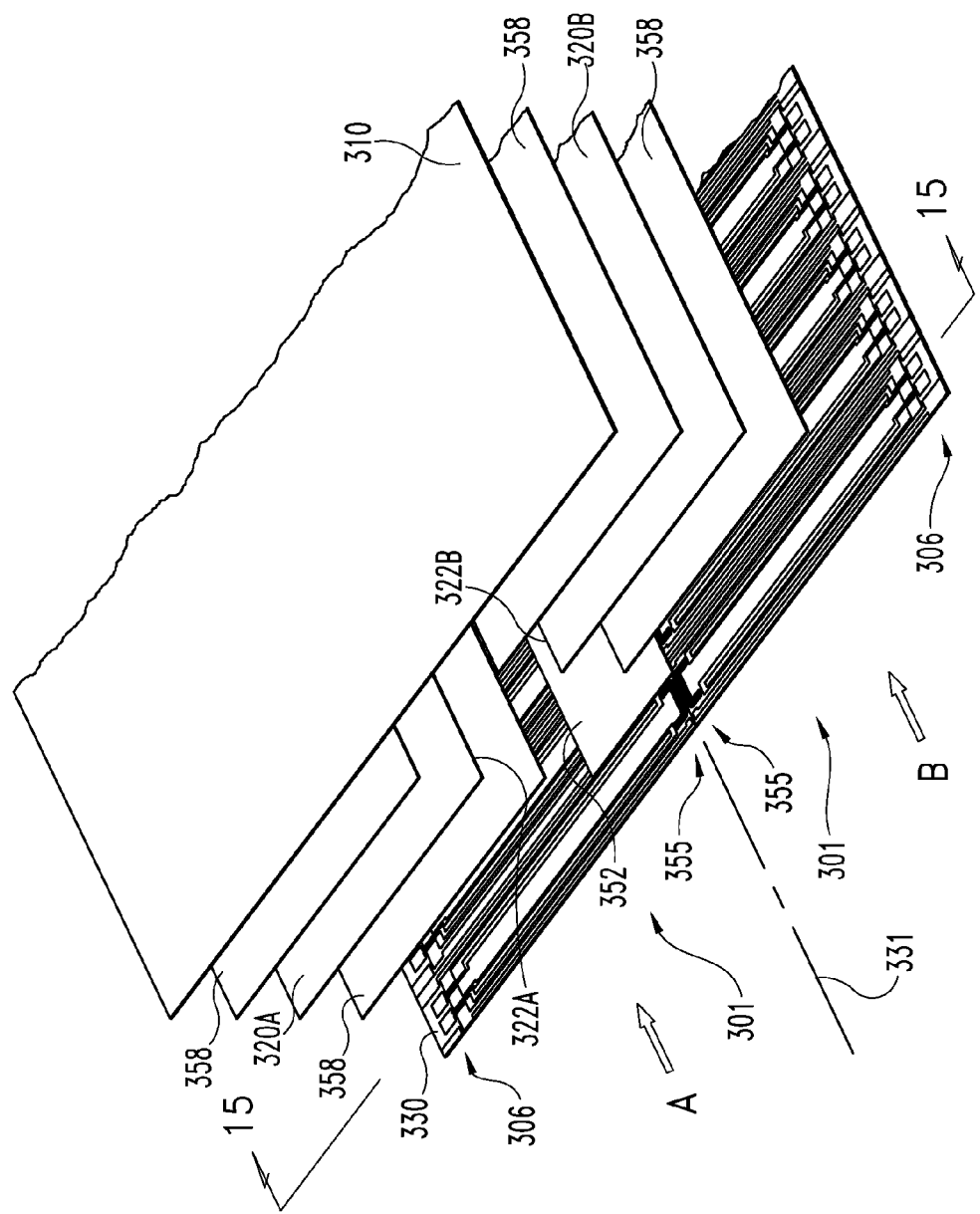
FIG. 13 is an exploded, fragmentary view of a plurality of biosensors prior to lamination during a 2-up manufacturing process according to yet another embodiment.
Figure 14:
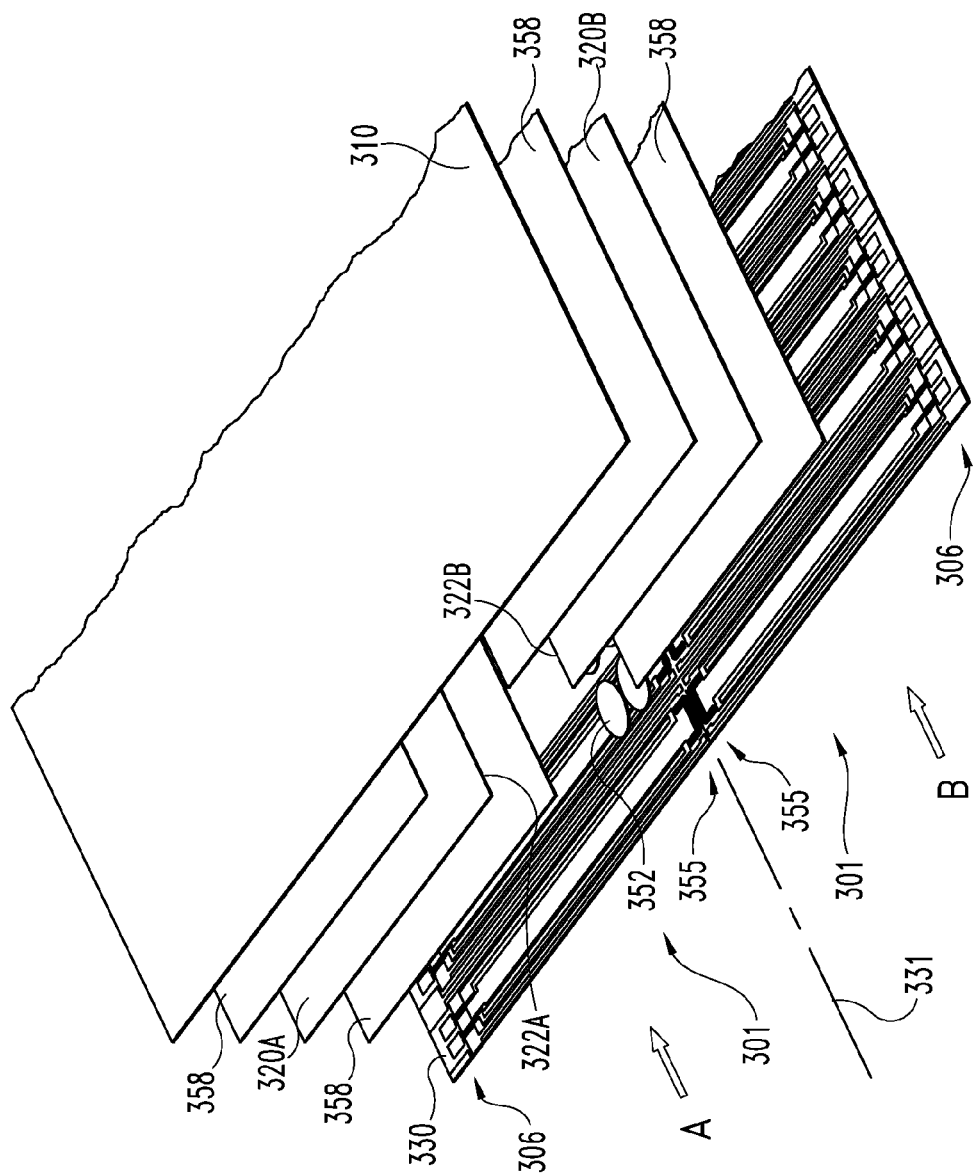
FIG. 14 is an exploded, fragmentary view of a plurality of biosensors prior to lamination during a 2-up manufacturing process according to yet another embodiment employing a discrete reagent layer deposition method.

FIG. 13 depicts an alternate manufacturing technique in which test strips are manufactured in a head-to-head arrangement, otherwise referred to as a "2-up" manufacturing technique. With the 2-up manufacturing process, a plurality of electrode patterns 301 are arranged in two columns (one set of electrode patterns in column A and one set in column B) on an elongated layer (tape) of the lower substrate 330. The electrode patterns in each column are arranged in a side-by-side manner, and as will be appreciated by a person of ordinary skill in the art in view of this disclosure, it is generally useful, although not required, that individual patterns in one column are generally opposite to individual patterns in the other column. The sample chamber electrode patterns 355 are located near each other and near the center of the lower substrate strip 330, with the contact pads 306 being spaced apart from one another and located near the opposite edges of the lower substrate strip. In the depicted embodiment, the electrode patterns are all similar; however in alternate embodiments at least some of the electrode patterns are different from other electrode patterns. A layer of the reagent 352 is applied in a stripe over the two sample chamber electrode patterns 355 simultaneously and dried to a thickness of, for example, two to ten micrometers (2-10 µm). An exemplary embodiment having more discrete deposition of the reagent layer 352 is illustrated in FIG. 14.

By employing a 2-up manufacturing technique, twice as many test strips are produced in the same length (as measured perpendicular to the test strip longitudinal axis 102, see FIG. 1) of the lower substrate tape 330 as compared to the embodiment depicted in FIG. 9, helping to reduce costs, reduce waste, and increase output.

Two elongated strips (tapes) form the spacer layers 320A and 320B, one for each column of electrode patterns. The spacer layers 320A and 320B are attached to the top of the lower substrate layer, either before or after application of the reagent. Edge guiding techniques can be used to align the edges 322A and 322B of the spacer layers 320A and 320B, respectively, a desired distance from the centerline 331 between columns A and B to create the desired sample chamber depth when the substrate layers are separated along the centerline 331.

The two spacer layer strips 320A and 320B may be formed from a single strip that is divided immediately prior to placement on the lower substrate layer, or may be formed from two separate strips of spacer material that are individually attached to the lower substrate layer 330.

An upper substrate layer 310 is attached to the top of the spacer layers 320A and 320B. The upper substrate layer 310 is a single, continuous layer. As such, the sample chambers in the two columns of head-to-head test strips are simultaneously formed when the upper substrate layer 310 is attached. In the illustrated embodiment, the lower substrate 330, the spacer layers 320A and 320B, and the upper substrate 310 are attached with the adhesive layers 358. The adhesive layers 358 may be elongated strips of PSA, adhesive tape, sprayed-on adhesive stripes, hot melt, co-extruded, or heat seal layers. Alternatively, spacer layers 320A and 320B are obviated by using a double sided adhesive tape as adhesive layer 358 having a thickness comparable to the thickness of spacer layers 320A and 320B. Alternative manners of fixing layers of a biosensor without adhesion layers include heat sealing, laser sealing, cold sealing, etc.

After the lower substrate 330, the reagent 352, the spacer layers 320A and 320B, and the upper substrate 310 are combined and laminated together, the sheet or roll is separated into individual test strips. The test strips in column A are separated from the test strips in column B (the sample chambers of the head-to-head oriented test strips are separated from one another approximately along the centerline 331) typically using a single cut along centerline 331, and the test strips in adjacent rows (side-by-side oriented test strips) are separated from one another between the electrode patterns. An alternative embodiment discussed below relating to FIGS. 17-18 employs multiple cuts.

Larger sample chamber depths (the distance between the column centerline 331 and the edges 322A and 322B of the spacer layers 320A and 320B) permit the use of more relaxed manufacturing tolerances when separating the test strips in column A from the test strips in column B (separating the head-to-head oriented test strips). Small inaccuracies in separating the sample chambers will not result in large variations in sample chamber size. However, larger sample chamber depths can result in larger aspect ratios and slower sample chamber filling, as discussed above.

As discussed above, when a broad field laser ablation technique is employed to form the electrode patterns 355, it is possible to configure the ablation technique so that multiple patterns are formed from each laser pulse. In a 2-up manufacturing process, the multiple patterns can be the facing patterns of columns A and B, and if the laser lens is sufficiently broad (and an appropriate mask is provided), the multiple patterns may include laterally adjacent patterns within a particular column as well as oppositely adjacent patterns between the columns. In one embodiment, four patterns are formed in a single pulse. In other embodiments, six or more patterns are formed in a single pulse. In addition to throughput advantages mentioned above, the ability to form the electrode patterns that oppose each other between columns A and B in a single ablation pulse also helps keep the spacing variation between the columns at a minimum. This helps control variation seen in the capillary width 146 by using the electrode pattern to position and control the placement of the spacers 120. The precise spacing of the electrode patterns can be used as a datum for locating and placing other components in the strip.

Again referring to FIGS. 1 and 2 for illustration, the upper substrate layer 110 and the lower substrate layer 130 are generally parallel about the chamber 150. The thickness and cantilever overhang of the upper substrate 110 and the lower substrate 130 can be selected to provide sufficient structural integrity and avoid bowing of the capillary chamber, which could occur during manufacture (such as during a portion of the singulation process to form individual test strips when columns of head-to-head electrode patterns are separated as in FIGS. 13 and 14) or during use and disrupt the T-shaped capillary flow pattern of the entering sample. The cantilever overhang of the upper substrate 110 is the overhang distance 140 between the front edge 122 of the spacer 120 and the upper substrate front edge 112. The cantilever overhang of the lower substrate 130 is the overhang distance 141 between the front edge 122 of spacer and the lower substrate front edge 132. Thinner substrate layers require stiffer materials and/or smaller cantilever overhangs to avoid bending of the substrate layer in the region of the sample chamber 150. Thicker substrate layers can accommodate larger cantilever overhangs without bending and compromising the functioning of the sample chamber, which may be exacerbated during the singulation process to form individual test strips when the upper and/or lower substrate layers are cut to form the forward edges of the test strip, for example, forward edges 112 and 132 as depicted in FIG. 2. In one example embodiment, the test strip has a cantilever overhang of no more than one and one-half millimeters (1.5 mm) and a thickness of at least one substrate is 3.8 mil. (0.0038 inches) thick so as to provide the requisite structural integrity of the sample chamber capillary channel. In order to facilitate reel-to-reel manufacturing, the upper 310 and the lower 330 substrate layers should be sufficiently flexible to accommodate being provided on rolls, but include enough structural rigidity to form a sample chamber. In one embodiment, a three (3) to fifteen (15) mil (0.003-0.015 inches) thick polymer layer is used for the upper 310 and the lower 330 substrate layers.

In a single column (1-up) manufacturing technique as depicted in FIG. 9, providing upper and lower substrate layers with disparate overhang distances (i.e. overhang distance 141 being unequal to overhang distance 140 from FIG. 2) is relatively straightforward wherein the upper or lower substrate layer is provided to extend a greater or lesser distance from edge 122. However, in a 2-up manufacturing technique, this is not so straightforward, but rather depends on the manner in which the columns A and B are separated.

Figure 15:
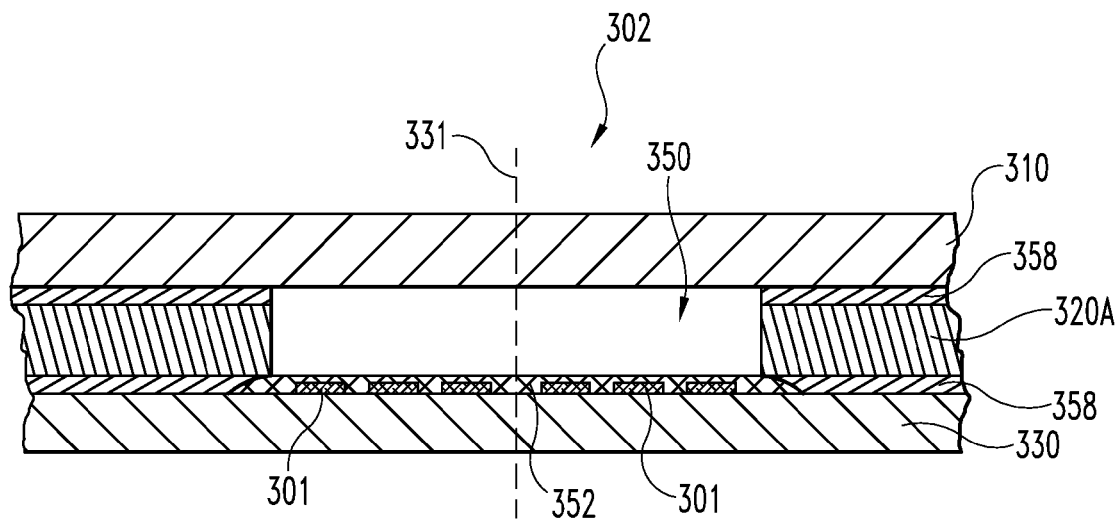
FIG. 15 is a fragmentary, sectional view of one of the test strip pairs depicted in FIG. 13 after lamination.
Figure 44:
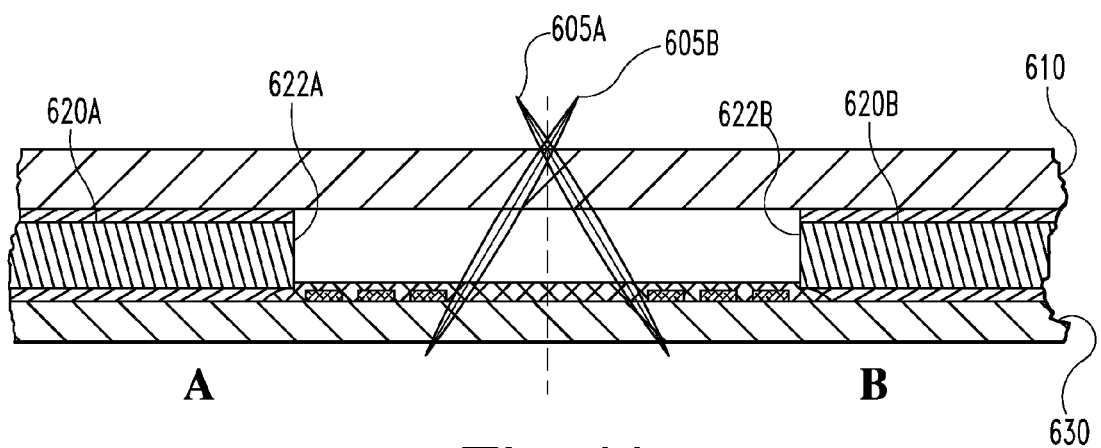
FIG. 44 is a fragmentary, cross sectional view of a two-cut singulation process for providing disparate overhang distances for the top layer and bottom layer substrates.
Figure 45:
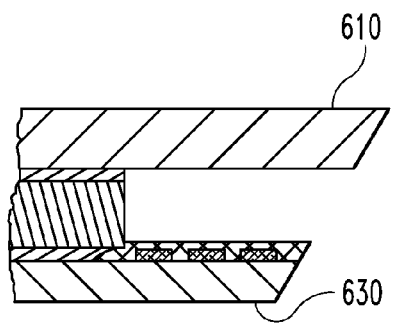
FIG. 45 is a fragmentary, cross sectional view showing the beveled end cuts and disparate overhang distances according to one embodiment.
Figure 46:
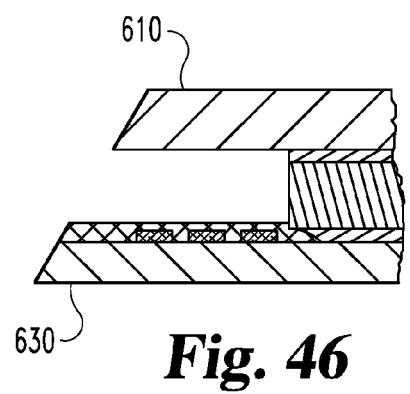
FIG. 46 is a fragmentary, cross sectional view showing the beveled end cuts and disparate overhang distances according to another embodiment.

In one embodiment, an angled cutting tool (angled with respect to the upper and/or lower substrate layer) is used to separate columns A and B. As shown in FIGS. 43-46, an angled cutting tool 605 produces test strips in which the upper substrate layer 610 and the lower substrate layer 630 extend different distances (have different cantilever overhangs) from the forward edges 622A and 622B of the spacer layers 620A and 620B. The overhang distances of column A are the converse of column B when a single angular cut is made, such as would result from a cut according to FIG. 43. When using two cutting tools 605A and 605B as shown in FIG. 44, two opposite angular cuts are made in opposite orientations so that the disparate overhang configuration is generally the same for strips singulated from each column. Illustrations of exemplary embodiments of disparate overhang distances are shown in FIGS. 45 and 46. Depicted in FIG. 15 is a cross-sectional view of a head-to-head test strip pair 302 after attaching the layers depicted in FIG. 13 to one another. The upper substrate 310 is attached to an adhesive layer 358, which is attached to the spacer layer 320A, which is attached to another adhesive layer 358, which is attached to lower substrate layer 330. Located atop lower substrate 330 are electrode pattern 301 and reagent layer 352. Sample chamber 350 is vertically defined in the space between upper substrate layer 310 and lower substrate layer 330. Sample chamber 350 is horizontally defined between the two adhesive layers 358 and the spacer layer 320A with the centerline 331 dividing the sample chamber 350.

Figure 16:
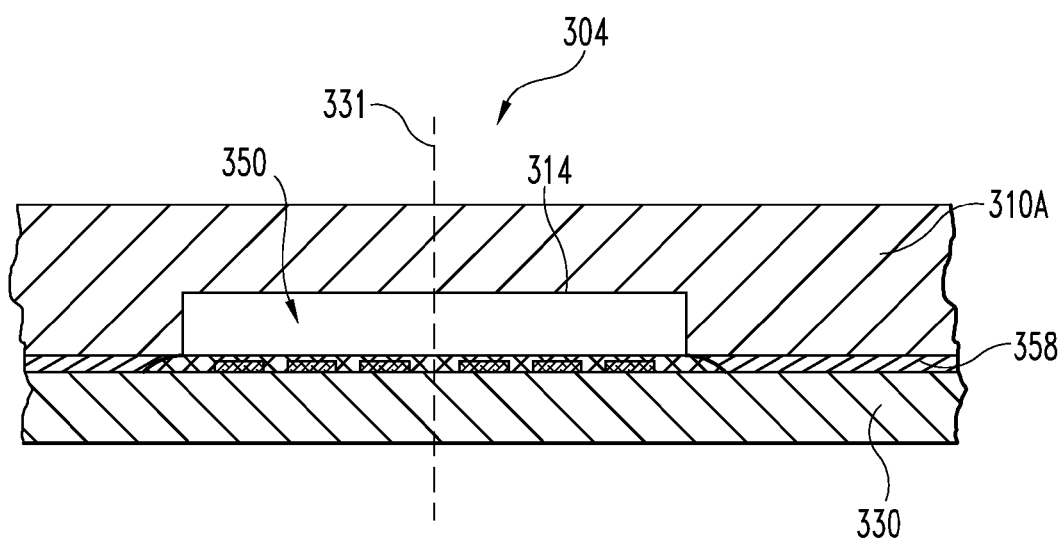
FIG. 16 is a fragmentary, sectional view of a test strip pair according to yet a further embodiment.

Depicted in FIG. 16 is a head-to-head test strip pair 304 with an upper substrate layer 310A according to another embodiment of the present invention. The use of the upper substrate layer 310A obviates the need for the spacer layer 320A depicted in FIG. 15. Upper substrate layer 310A includes a recess, for example groove 314, which, together with the lower substrate layer 330 and the adhesive layer 358, define sample chamber 350. Sample chamber 350 is divided by centerline 331. The depth and width of groove 314 can be accurately controlled during the manufacturing process. As such, the size of sample chamber 350 can be accurately controlled and the need to include, align and attach a spacer layer 320A is eliminated. In one embodiment, groove 314 is formed by laser ablation. In alternate embodiments, groove 314 is formed using a calendering process, which allows the finished test strips to maintain a flat profile for efficient stacking. In still further embodiments, groove 314 is formed by skiving or by embossing.

Figure 17:
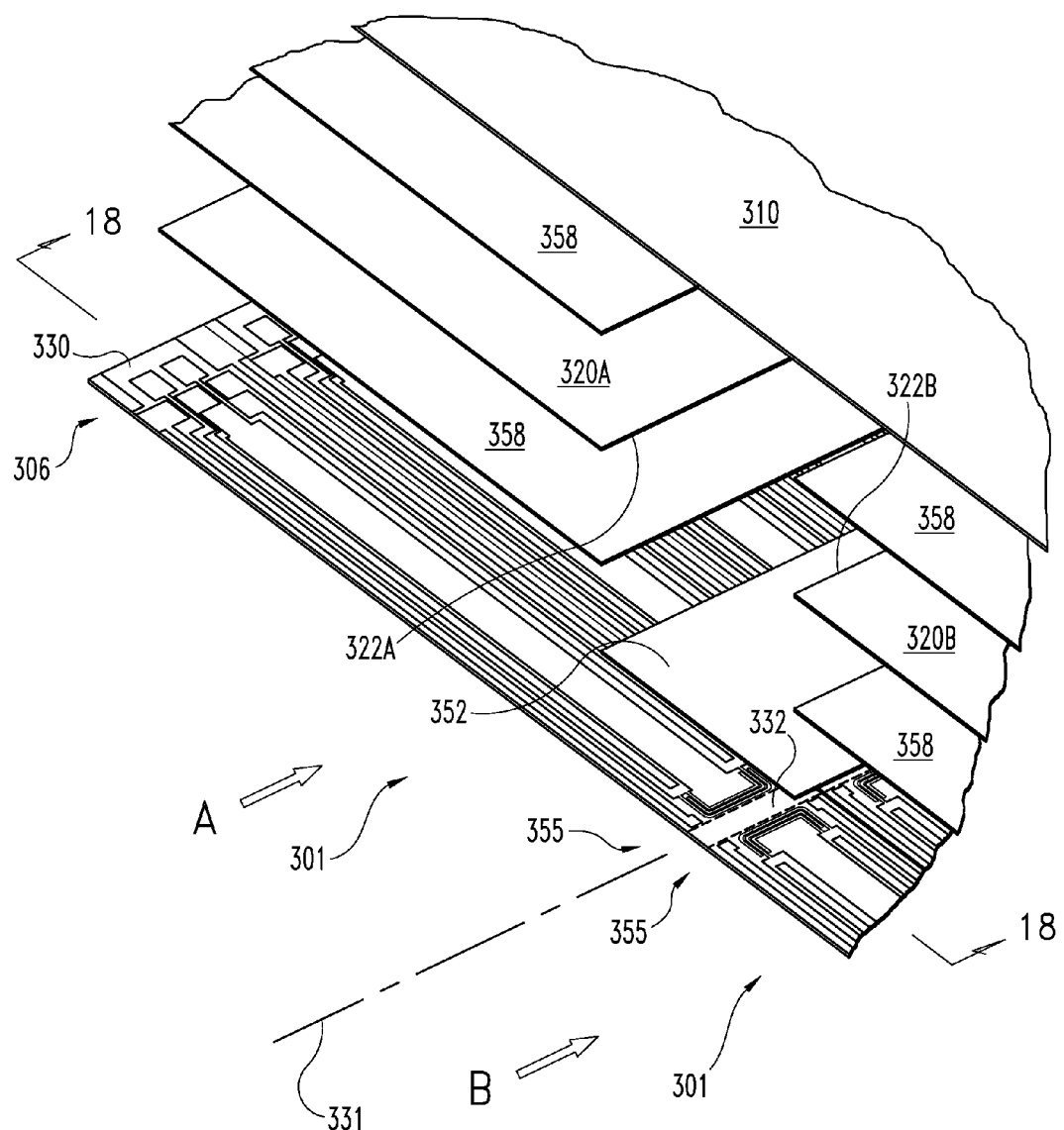
FIG. 17 is an exploded, fragmentary view of a plurality of biosensors prior to lamination during a 2-up manufacturing process according to yet another embodiment including a margin separating Columns A and B.
Figure 18:
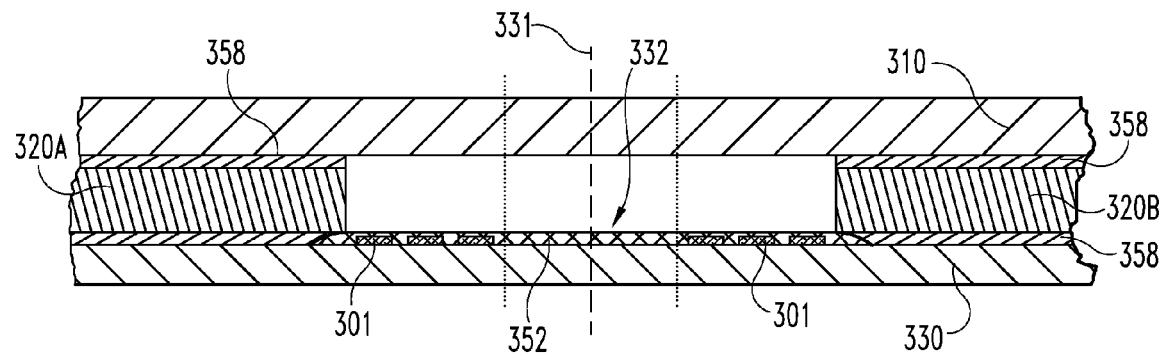
FIG. 18 is a fragmentary, sectional view of one of the test strip pairs depicted in FIG. 17 after lamination.

Depicted in FIG. 17 is an alternate embodiment manufacturing technique (which may also be referred to as a modified 2-up manufacturing process) for manufacturing test strips in a head-to-head arrangement. The electrode patterns 355 in FIG. 17 are spaced further apart than the electrode patterns 355 in FIG. 14 and the increased distance defines a margin 332 (sometimes referred to as an alley) extending between the two sets of electrode patterns 355. After the lower substrate 330, the reagent 352, the spacer layers 320A and 320B, the adhesive layers 358 and the upper substrate 310 are combined and laminated together, the test strips in column A are separated from the test strips in column B and the test strips in adjacent rows are separated from one another between the electrode patterns.

In one embodiment, three cuts are made to separate column A from column B and form the forward edges of the test strips, for example, the forward edges 112 and 132 depicted in FIG. 2. A cut is made in the margin near the centerline 331. Another cut is made to form the forward edges of the test strips in column A and still another cut is made to form the forward edges of the test strips in column B.

In another embodiment, two cuts are made to separate column A from column B and form the forward edges of the test strip. A cut is made adjacent the electrode patterns 355 in column A to form the forward edge of the test strips in column A and separate column A from the margin 332 and column B. Another cut is made to form the forward edge of column B and separate column B from the margin 332.

The embodiments with margin 332 between electrode patterns 355 (described with respect to FIG. 17) can be useful when a single cut to separate the test strips in columns A from the test strips in columns B and form the sampling ends of the test strips is not preferred. For example, in certain embodiments, the strength of the upper substrate layer 310 and/or the lower substrate layer 330 is insufficient to allow a single cut without compromising the integrity of the sample chamber.

Figure 20:
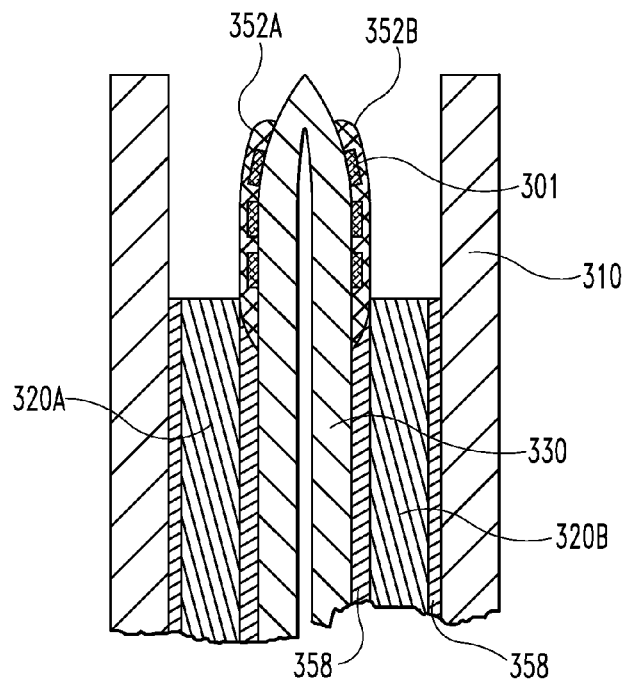
FIG. 20 is a fragmentary, sectional view of one of the test strip pairs depicted in FIG. 19 after lamination and after preparation for use as a dual-use biosensor according to embodiments disclosed herein.
Figure 19:
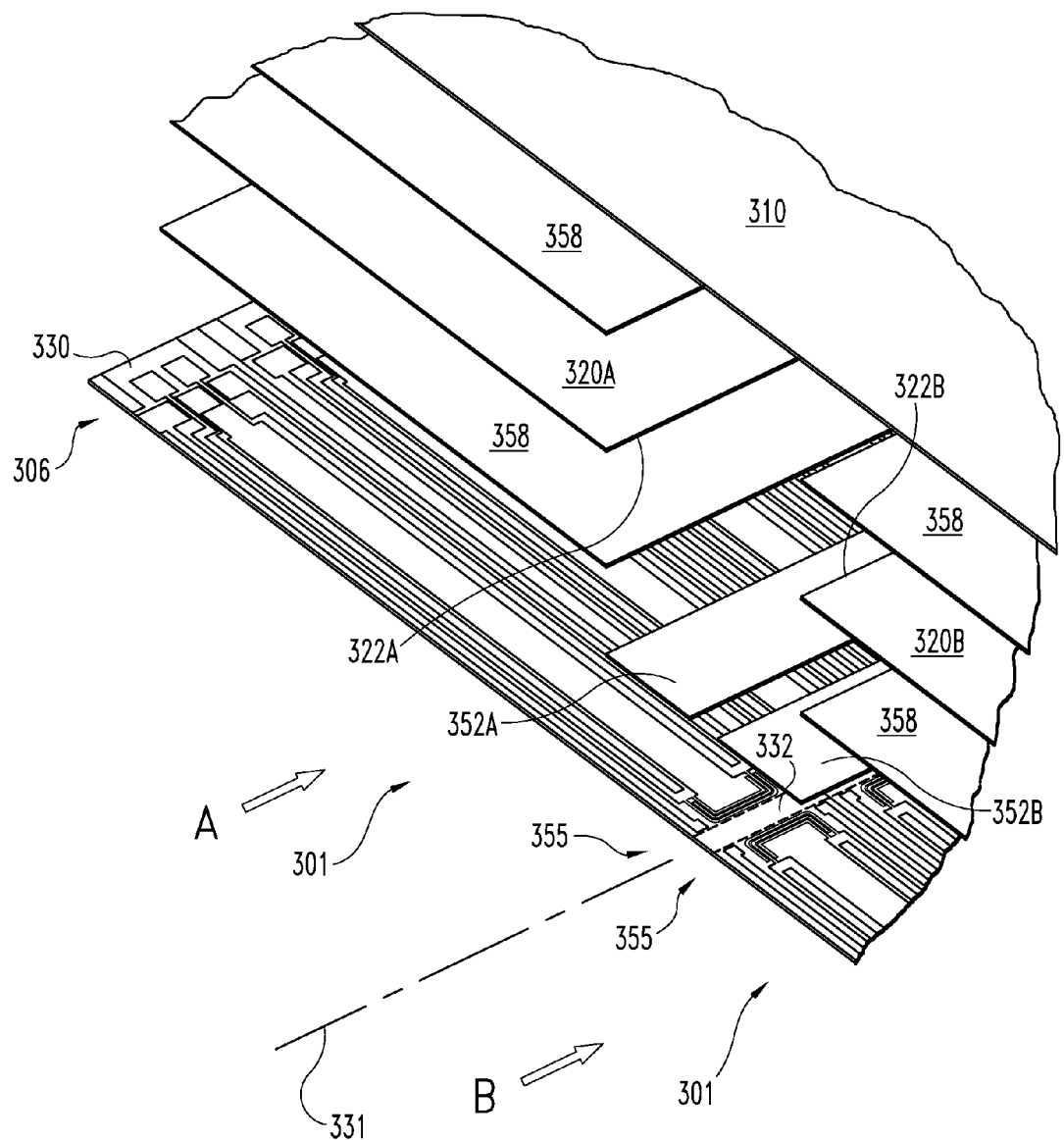
FIG. 19 is an exploded, fragmentary view of a plurality of biosensors prior to lamination during a 2-up manufacturing process according to yet another embodiment employing a discrete reagent layers over the electrode patterns of each of Column A and Column B.
Figure 21:
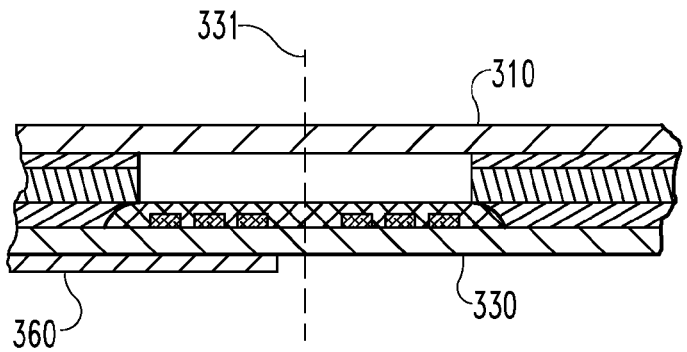
FIG. 21 is a fragmentary, sectional view of an alternative embodiment for making a dual-use biosensor.

Referring to FIGS. 19 and 20, in an alternate embodiment the layer 352 of reagent material includes two different reagents—one positioned over the electrode patterns 355 of column A and the other reagent positioned over the electrode patterns 355 of column B. In this embodiment, the head-to-head pair of electrode patterns remain attached to one another (the test strips in Column A remain attached to the test strips in column B) while the test strips in adjacent rows (side-by-side oriented test strips) are separated. In other words, the test strips in column A are not fully separated from the test strips in column B, and test strip pairs are formed with each pair of test strips arranged in a head-to-head manner. Each test strip pair may be folded to place the contact pads of the test strip from column A adjacent the contact pads of the test strip from column B, and to place the sampling end of the test strip from column A adjacent to and facing the same direction as the sampling end of the test strip from column B. Using this type of head-to-head test strip pair, a dual-use biosensor is provided in which a user can apply a sample of bodily fluid to both test strips simultaneously. Since the reagents in the two sample chambers are different, each sample chamber will test for a different analyte, and two separate tests will be performed after lancing the skin only once. As an example, one test strip could test for glucose while the other test strip tests for ketones or triglycerides. The relatively small size of the disclosed sample chambers further enhances the ability to perform two tests with a single droplet of bodily fluid since a single lancing of the skin is more likely to produce sufficient fluid to perform two tests. In one embodiment, a blood filtering media is provided within the dual sample chamber area prior to folding the pair together, in order to prevent blood and reagent mixing between the chambers.

It should be appreciated that the sample chambers in each of the head-to-head oriented pair of test strips should be exposed when the pair of test strips are bent along centerline 331. Alternative manufacturing techniques can be used to ensure both sample chambers are exposed. For example, in one embodiment, one of the substrate layers, e.g. the top layer, is fully separated along centerline 331 during manufacture while the other substrate layer, e.g. the bottom layer, is either unmodified or modified to predictably bend about centerline 331. In an alternate embodiment, one of the substrate layers is modified, such as through perforation or partial cutting to be easily separated by the user along centerline 331 while the other substrate is modified, such as by scoring, denting or crimping, to predictably bend or separate about a straight line, for example, centerline 331. In still another embodiment, both the upper substrate layer 310 and the lower substrate layer 330 are modified to allow the head-to-head test strips to be folded in either direction, i.e., the user may choose to bend the head-to-head pair of test strips to have the upper substrate layers 310 of the two test strips positioned adjacent one another or to have the lower substrate layers 330 of the two each test strips positioned adjacent one another.

Figure 22:
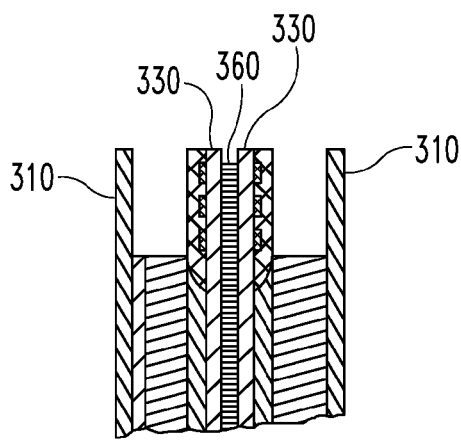
FIG. 22 is a fragmentary, sectional view of a completed dual-use biosensor according to FIG. 21

FIGS. 21-25 show further alternative embodiments of a dual-use biosensor. According to FIGS. 21 and 22, an adhesion layer 360 can be provided on the bottom layer 330 on only one side of centerline 331. Columns A and B are then fully separated about the centerline 331 and affixed by adhesion layer 360 in an orientation similar to the folded-over embodiment above (FIG. 20), as shown in FIG. 22. In such embodiments, potential variability from having the user fold the bottom layer is avoided, as is any effort of perforating the top layer and/or scoring, denting or crimping the bottom layer to define a folding line.

Figure 23:
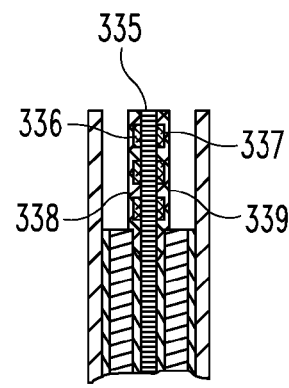
FIG. 23 is a fragmentary, sectional view of another alternative embodiment of a dual-use biosensor.

In the alternative embodiment of FIG. 23, a tri-laminate construction is provided in which a middle layer 335 having electrode patterns 336 and 337 disposed on its opposite surfaces. Two different reagents 338 and 339 can be provided respectively on each electrode pattern to form a dual-use biosensor. The remaining construction of the biosensor is similar to previously described embodiments, i.e. a spacer layer and a top or cover layer are affixed to the middle layer to define sample chambers on each side of the middle layer.

Figure 24:
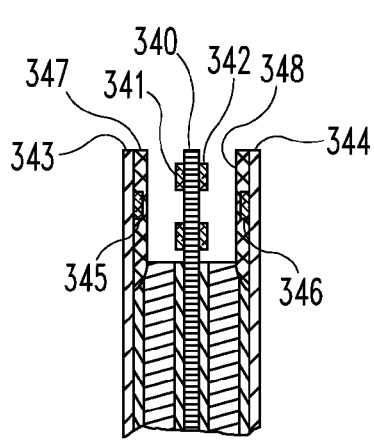
FIG. 24 is a fragmentary, sectional view of yet another alternative embodiment of a dual-use biosensor.

In the further alternative embodiment of FIG. 24, a middle layer 340 is provided having electrode patterns 341 and 342 on its opposite surfaces. The top or cover layers 343 and 344 have electrode patterns 345 and 346 formed thereon such that the completed construction provides a dual-use biosensor having sample chambers comprising a facing electrode configuration. As depicted in FIG. 24, the electrode patterns 345 and 346 on the cover layers 343 and 344 comprise the working electrode patterns to which reagent layers 347 and 348 are applied, whereas the electrode patterns 341 and 342 on the opposite surfaces of the middle layer 340 comprise the counter electrode patterns. Alternatively, the counter electrodes may be provided on each of the cover layers 343 and 344 and the working electrode and reagent may be provided on the middle layer 340. In these two alternate embodiments, the sample chamber on each side of the dual-use biosensor no longer has the electrode pattern provided on only one surface of the chamber (i.e. co-planar).

Figure 25:
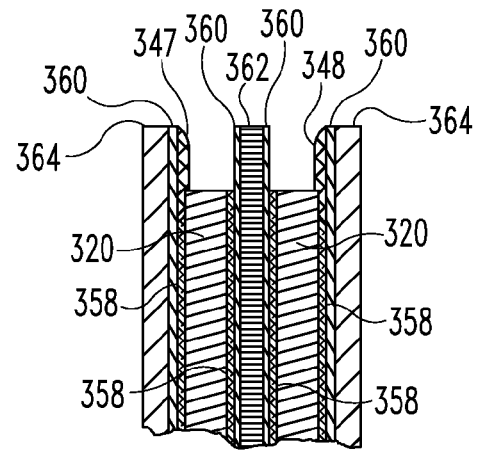
FIG. 25 is a fragmentary, sectional view of yet another alternative embodiment of a dual-use biosensor.
Figure 48:
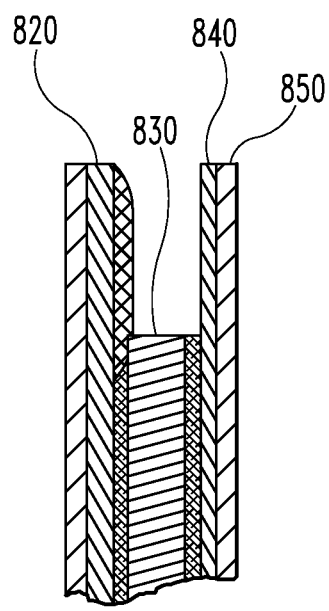
FIG. 48 is a fragmentary, cross sectional view of an alternative embodiment of a biosensor according to the present invention having a facing electrode configuration.

In yet another embodiment shown in FIG. 25, rather than include the step of forming the working electrode and counter electrode into particular patterns, the respective conductive material 360 forming the metalized surfaces of the middle layer 362 and the top/cover layers 364 is left unablated such that there is no particular electrode patterning. Similar embodiments are discussed further below with regard to FIG. 48 showing a single-use biosensor having undefined electrodes in a facing electrode configuration.

The embodiments of dual-use biosensors discussed herein comprise a single biosensor that has two different electrochemical analyses which can be performed. Each sample chamber for such a dual-use biosensor has a different reagent layer configured for a particular analysis. During manufacture in a 2-up process, precise and discrete reagent layer deposition, such as by ink jetting, is used in order to provide the different reagent layers either in a continuous stripe or discretely over each electrode pattern. For the facing electrode configuration embodiments shown, e.g. FIGS. 24 and 25, discrete metal deposition techniques can also be utilized in order to provide electrodes of differing materials, such as a silver-silver chloride (Ag/AgCl) reference electrode. The advantages of using a reference electrode during the electrochemical analysis are known in the art. Of course, discrete metal deposition is not required to provide a facing electrode configuration comprising different electrode materials. For example, copper and gold coated substrates may be formed using similar atomic vapor deposition methods. In contrast, however, a Ag/AgCl reference electrode material cannot be deposited using such a method.

Different electrode patterns may also be used for testing the sample fluid. For example, FIG. 26 depicts an electrode pattern 455A with a counter electrode 460A, a working electrode 462A and the two sample sufficiency electrodes 464A extending to an edge 432A of a lower substrate layer 430A. Extending the electrodes to the edge 432A of the lower substrate layer 430A can be advantageous when manufacturing test strips in a head-to-head configuration (see, e.g., FIG. 13). Relaxed manufacturing tolerances and increased manufacturing efficiency can be realized when separating two head-to-head test strips to form an edge 432 since the precise location of the edge 432 is not as critical as with electrode patterns that vary along the longitudinal axis 402A.

FIG. 27 depicts an electrode pattern 455B with a counter electrode 460B, a working electrode 462B and two sample sufficiency electrodes 464B, which all extend to the edge 432B of lower substrate layer 430B. The sample sufficiency electrodes 464B also extend to the outside edges of the lower substrate layer 430B, which can be advantageous during manufacture. For example, relaxed tolerances and increased manufacturing efficiencies may be realized when separating test strips that are arranged side-to-side during the manufacturing process since the precise location of the side edges are not as critical as with electrode configurations where the electrodes are spaced a small distance from the side edges.

FIG. 28 depicts an electrode pattern 455C with a lower substrate layer 430C with two sample sufficiency electrodes 464C that extend to the edge 432C and also extend to the outer edges of lower substrate layer 430C. However, a counter electrode 460C and a working electrode 462C do not extend to the edge 432C of the lower substrate layer 430C, which can have advantages in limiting the ability of the user to adversely affect the test results by accidentally touching the working 462C and the counter 460C electrodes during testing.

FIG. 29 depicts still another embodiment electrode pattern 455D formed on a lower substrate 430D. The electrode pattern 455D includes a single counter electrode 460D and a single working electrode 462D bracketed by the two sample sufficiency electrodes 464D.

FIG. 30 depicts a sample chamber electrode pattern 455E with a single sample sufficiency electrode 464E and a counter electrode 460E located on the opposite side of the sample chamber and bracketing the working electrode 462E therebetween. In this embodiment, dual dedicated sample sufficiency electrodes are not required with the counter electrode being able to act as a sample sufficiency electrode.

The sample chamber electrode pattern 455F depicted in FIG. 31 does not include dedicated sample sufficiency electrodes, but rather includes the two counter electrodes 460F located near the outside edges of the sample chamber and bracketing the working electrode 462F therebetween. Here, the counter electrodes can also function as sample sufficiency electrodes.

Depicted in FIG. 32 is an embodiment in which the width of the sample chamber 450G is less than the width of the test strip adjacent sample chamber 450G, which is labeled as the spacer layer 420G in FIG. 32. Located in sample chamber 450G are a T-shaped working electrode 462G, a counter electrode 460G, and a dedicated sample sufficiency electrode 464G.

Figure 33:
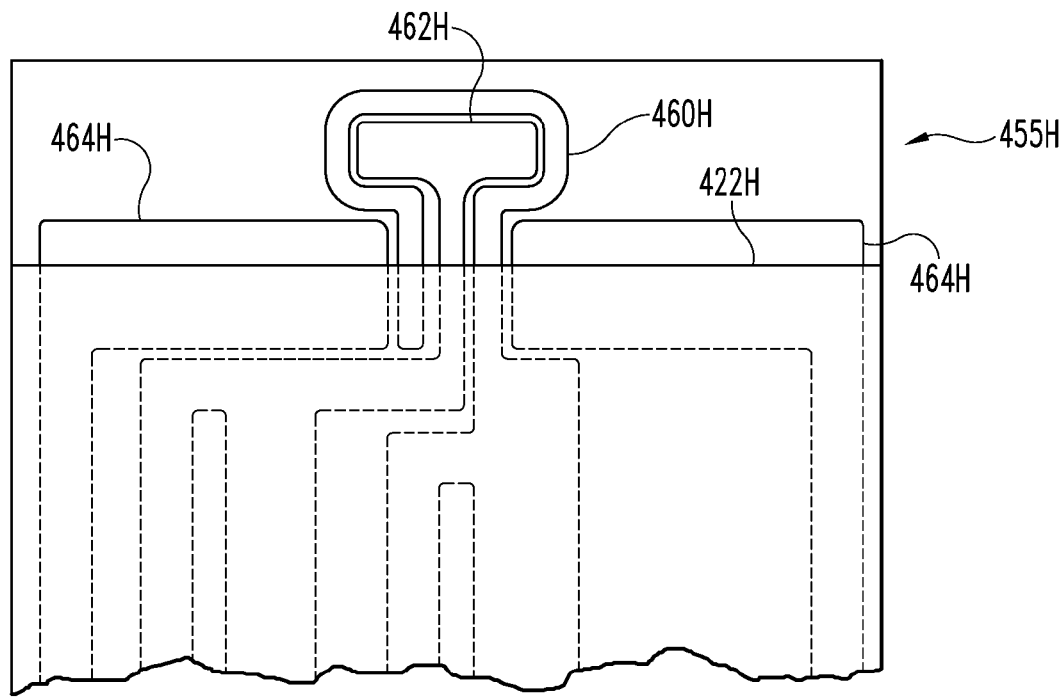
FIG. 33 is a fragmentary, top plan view of an alternate sampling end electrode pattern according to another embodiment.

FIG. 33 depicts an embodiment with an electrode pattern 455H that includes a generally T-shaped working electrode 462H surrounded by a counter electrode 460H. Two sample sufficiency electrodes 464H are also provided and are positioned near the spacer layer edge 422H. Placing the sample sufficiency electrodes 464H behind the working 462H and the counter 460H electrodes helps ensure that the working 462H and the counter 460H electrodes are completely covered before testing initiates. It also provides more area for the working electrode and counter electrode to cover, which allows for the wider 'hammerhead' design of the working electrode to increase the exposed working electrode area in the sample chamber relative to the connective neck that extends from the working electrode under the edge 422H. The result of which is minimal impact on working electrode area variance (and thus measured current response) due to variation in placement of the edge 422H relative to the electrode pattern 455H.

Figure 34:
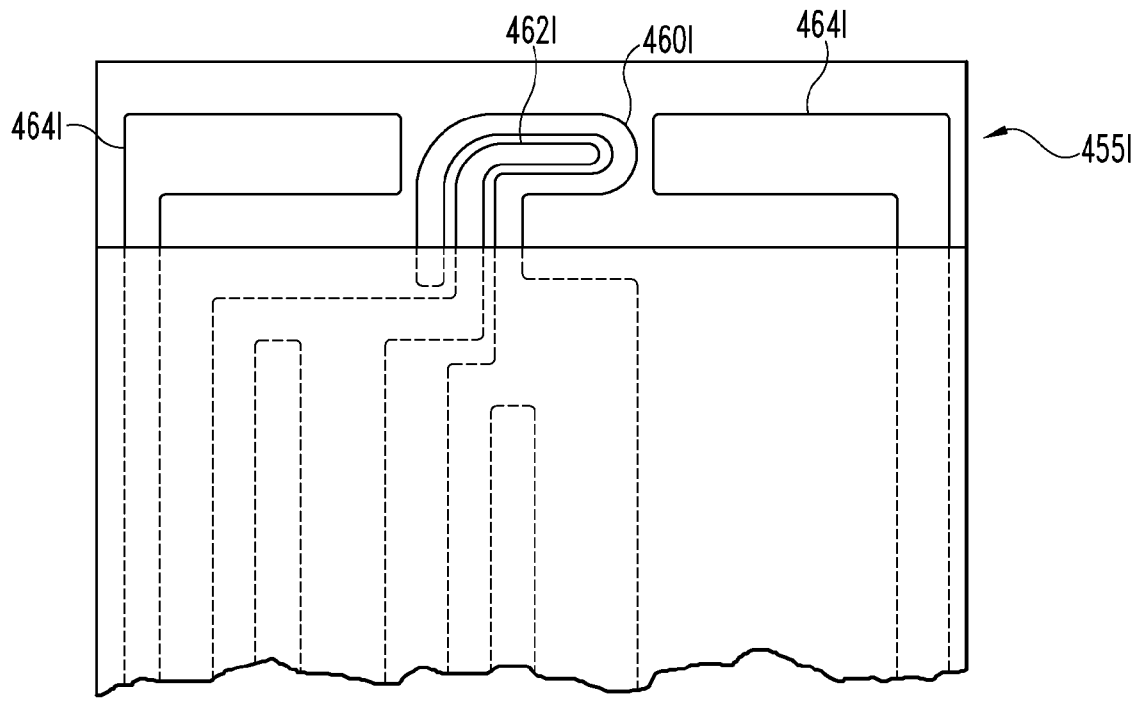
FIG. 34 is a fragmentary, top plan view of an alternate sampling end electrode pattern according to still another embodiment.

FIG. 34 depicts an alternate embodiment with an electrode pattern 455I including a working electrode 462I that is generally L-shaped and a counter electrode 460I that surrounds the working electrode 462I. The sample sufficiency electrodes 464I bracket the working 462I and the counter 460I electrodes. The working 462I and the counter 460I electrodes span only a portion of the sample chamber width (for example approximately one-quarter (¼) of the testing chamber width in the depicted embodiment) requiring a sample size smaller than that required to fill the entire sample chamber.

Figure 35:
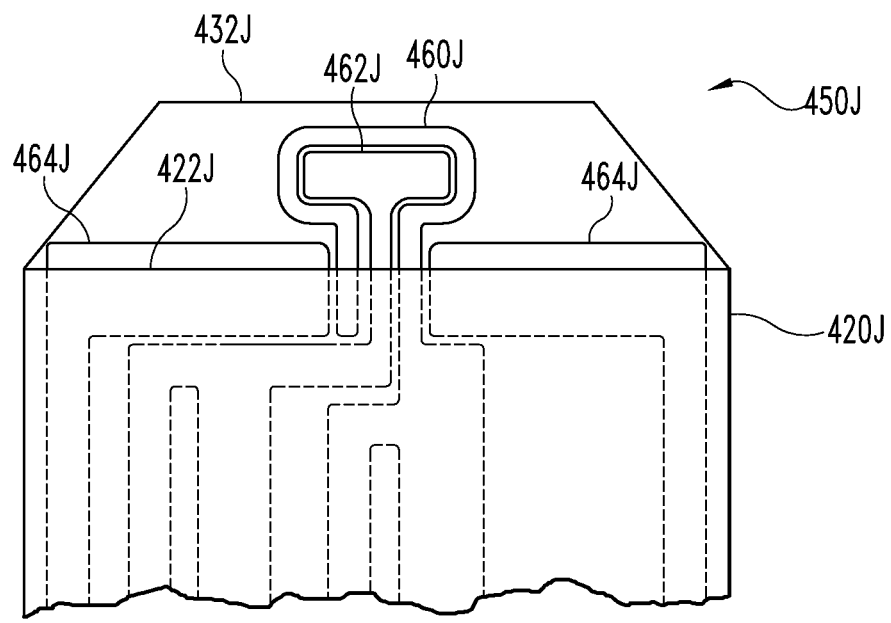
FIG. 35 is a fragmentary, top plan view of an alternate sampling end configuration according to yet another embodiment.

FIG. 35 depicts an embodiment where the lateral edges of the sample chamber 450J are angled inwardly relative to the lateral edges of the spacer layer 420J, and the width of the lower substrate layer edge 432J is less than the width of the spacer layer edge 422J. The shape of the sample chamber 450J may be referred to as a "rocket" shape and provides for two-dimensional filling (similar to FIGS. 7-8F) while having a volume that is less than that of a rectangular sample chamber with the same depth and a width equal to the width of the edge 422J of the spacer layer 420J. Located within sample chamber 450J are a working electrode 462J, a counter electrode 460J, and two sample sufficiency electrodes 464J. Although depicted as straight lines, it should be appreciated that the edges of the sample chamber 450J need not be straight lines, but may also include, for example, multi-segmented and curved lines.

Figure 36:
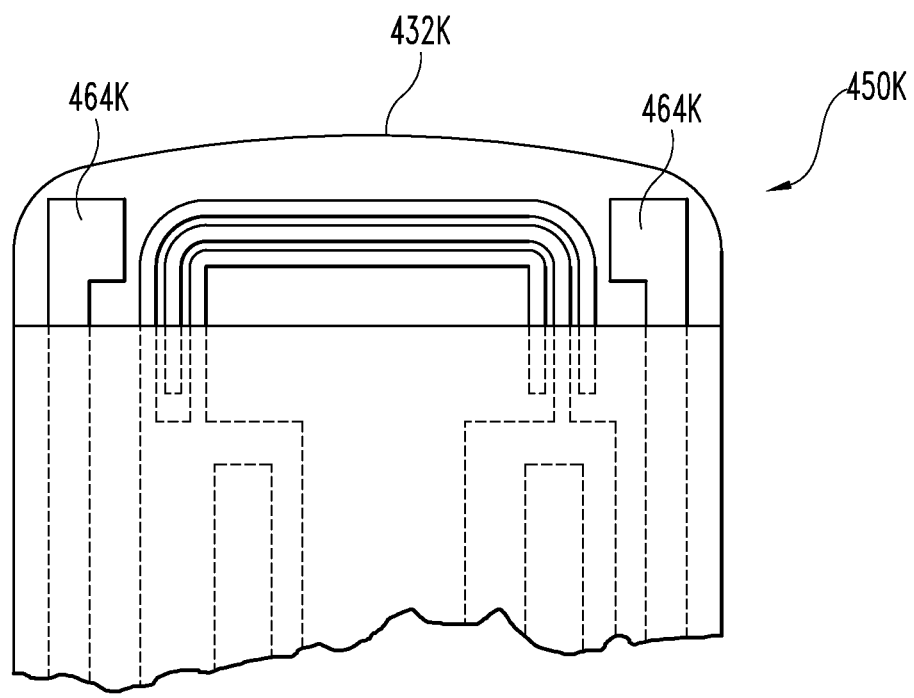
FIG. 36 is a fragmentary, top plan view of an alternate sampling end configuration according to another further embodiment.

FIG. 36 depicts still another embodiment where at least one edge of the sample chamber 450K is curved. The curved nature of the edge 432K of the sample chamber 450K can be more comfortable for user while providing for two-dimensional filling (similar to FIGS. 7-8F). The volume of the sample chamber 450K is less than that of a rectangular sample chamber with the same depth (as measured from the mid point between the sample sufficiency electrodes 464K) and a width equal to the width of the spacer layer edge 422.

In certain embodiments of the present invention, the lower substrate layer (e.g., lower substrate layer 130) is generally constructed of a 10 mil (0.01 inch) strip of insulating substrate, for example a polyethylene terephthalate (PET, for example, Melinex® manufactured by E.I. Du Pont de Nemours & Co.), polyethylene naphthalate (PEN), polyvinyl chloride (PVC), polyimide (PI) or polycarbonate (PC) film. In other embodiments, the electrodes and electrode patterns (e.g., sampling end electrode pattern 155) are formed on top of the lower substrate layer using laser ablation or other techniques appropriate for creating well-defined electrode patterns in a relatively small test area. The electrodes may be made from, for example, sputtered, printed or ink jetted gold, palladium, platinum or carbon. The spacer layer (e.g., spacer layer 120) can be opaque and can include printing or labeling, such as labeling that identifies the test strip and/or directions for using the test strip.

Figure 37:
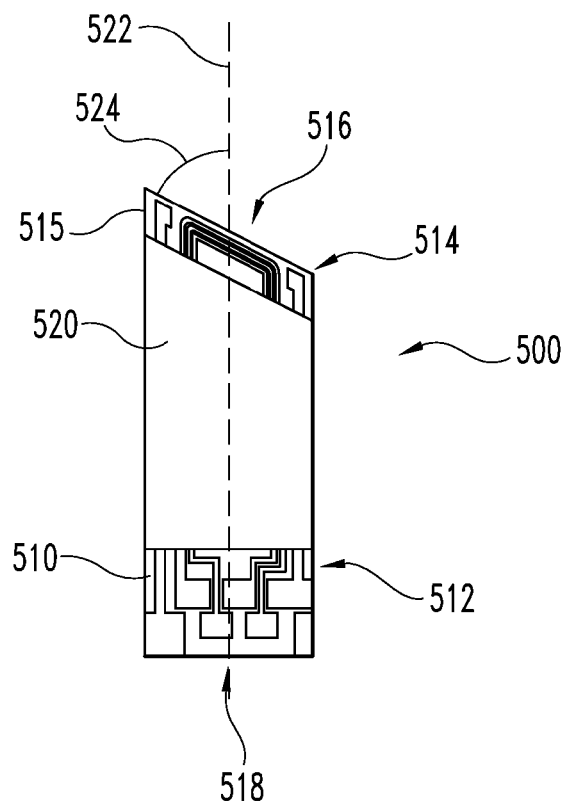
FIG. 37 is a top plan view of a test strip singulated from the sheet of test strips shown in FIG. 38.

Depicted in FIG. 37 is a test strip 500 according to another embodiment of the present invention. Test strip 500 includes a lower substrate layer 510. Test strip 500 also includes a contact pad pattern 512 and an electrode pattern 514 provided on top of the lower substrate 510. A reagent layer 515 (which is depicted as being transparent) overlies electrode pattern 514 and the portion of lower substrate layer 510 in the vicinity of the electrode pattern 514 not covered by electrode pattern 514. The electrode pattern 514 is located at the sampling end 516 while the contact pad pattern 512 is located at the test meter connection end 518. A spacer layer 520 overlies the substrate layer 510, contact pad pattern 512 and electrode pattern 514. Test strip 500 further includes an upper substrate layer, although the upper substrate layer is not depicted in FIG. 37 to provide a clearer view of the electrodes and spacer layer.

The sampling end 516 is not perpendicular to the longitudinal axis 522 of test strip 500. Instead, sampling end 516 is inclined at a nonperpendicular angle 524 from the longitudinal axis 522, i.e., angle 524 is not equal to ninety (90) degrees. For a specified lateral test strip width, the angled sampling end 516 presents a longer edge for the user to apply a sample than a typical test strip with a sampling end that is perpendicular to the longitudinal axis. Some patients find the longer, angled edge easier to use, especially patients with reduced manual dexterity. The longer sampling edge of the angled sampling end 516 can be particularly advantageous when used with a relatively narrow test strip, for example, test strips with a lateral width equal to five millimeters (5 mm) or less.

Figure 38:
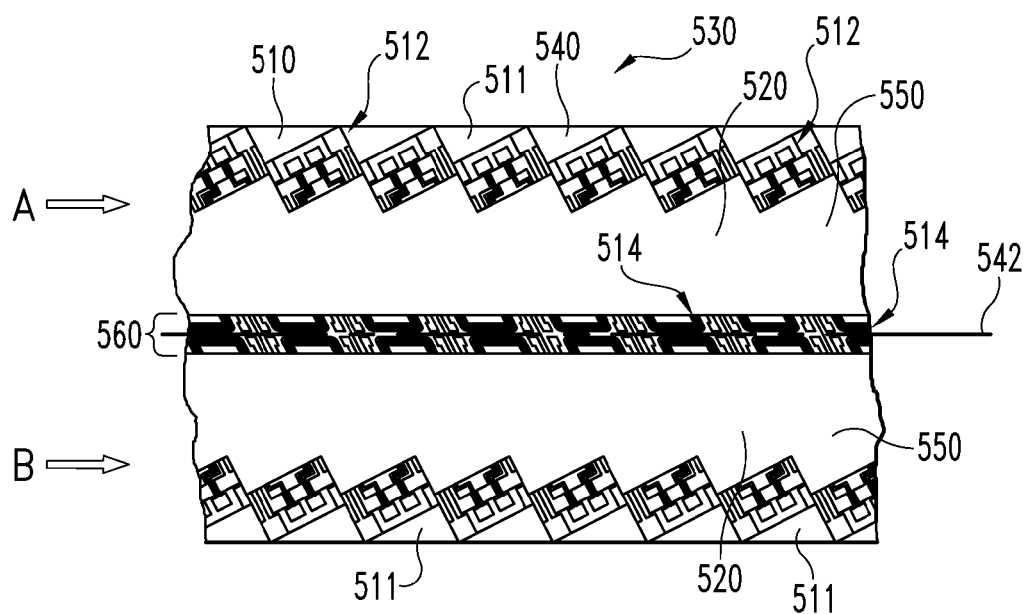
FIG. 38 is a fragmentary, top plan view of a sheet of biosensors manufactured in a 2-up manufacturing process according to yet another embodiment.

Depicted in FIG. 38 is a plurality of partially constructed test strips 530 during a manufacturing process for producing test strip 500 according to one embodiment of the present invention. Contact pad pattern 512 and sampling end electrode pattern 514 are formed on an elongated tape 540 of lower substrate 510. The contact pad patterns 512 and electrode patterns 514 are formed on top of the elongated lower substrate tape 540 using, for example, laser ablation techniques. The tape 540 defines a longitudinal axis 542 and the electrode patterns (which include electrode pattern 514 and contact pad pattern 512) are angled with respect to the longitudinal axis 542. Two elongated tapes 550 of material that form spacer layer 520 are layered on top of the electrode patterns and the lower substrate tape 540. A reagent layer stripe 560 (depicted as being transparent) is layered over the electrode patterns 514 and the elongated lower substrate tape 540 that form the sample chambers. A cutting device that produces a ratchet-cut removes the excess material 511 of the lower substrate tape 540. A similar ratchet cutting device may also be used to produce an edge of each elongated spacer layer tape 550.

After the elongated spacer tape 550 and reagent layer stripe 560 are attached to the elongated lower substrate layer 540 and the electrode patterns, an elongated upper substrate tape is applied (not depicted in order to show detail of the other portions of the test strips). The test strips are separated from one another using a singulation process that separates the test strips in column A from the test strips in column B along the longitudinal axis 542. Adjacent test strips are separated also by a straight cut along the lateral sides of each strip, although the excess material 511 is first separated from each column with, for example, a ratchet-cut technique.

Figure 41:
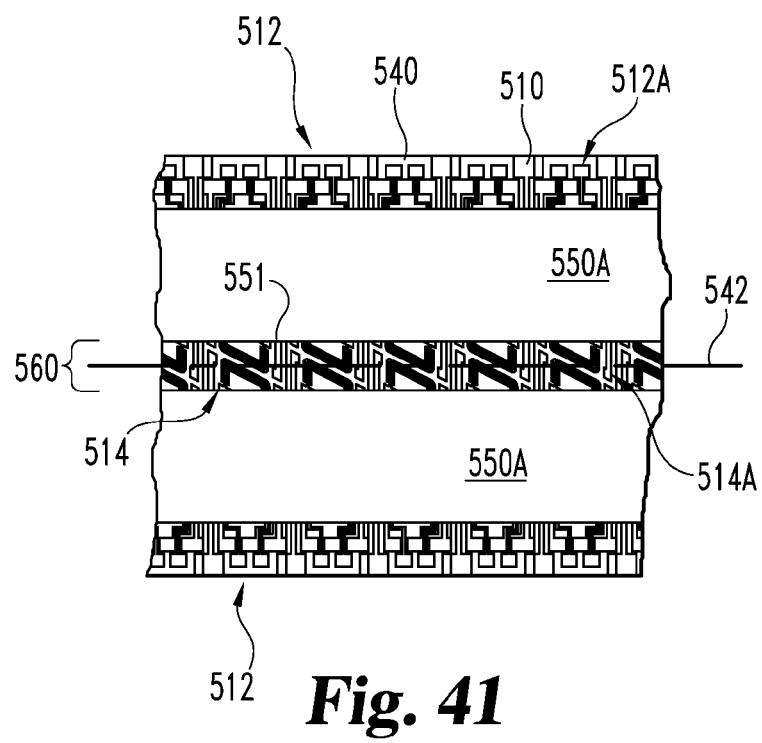
FIG. 41 is a fragmentary, top plan view of a sheet of biosensors manufactured in a 2-up manufacturing process according to still another embodiment.
Figure 42:
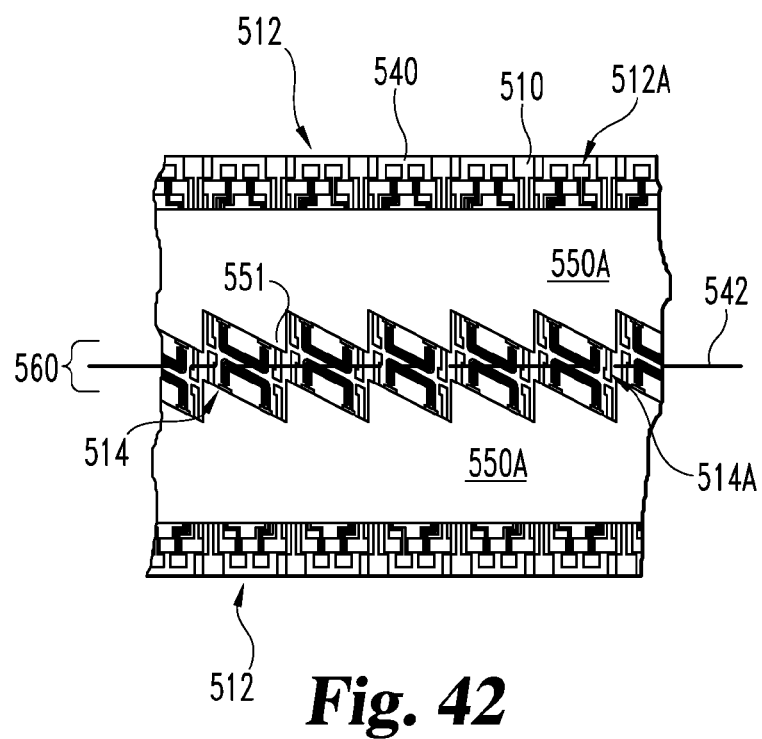
FIG. 42 is a fragmentary, top plan view of a sheet of biosensors manufactured in a 2-up manufacturing process according to yet another embodiment.
Figure 43:
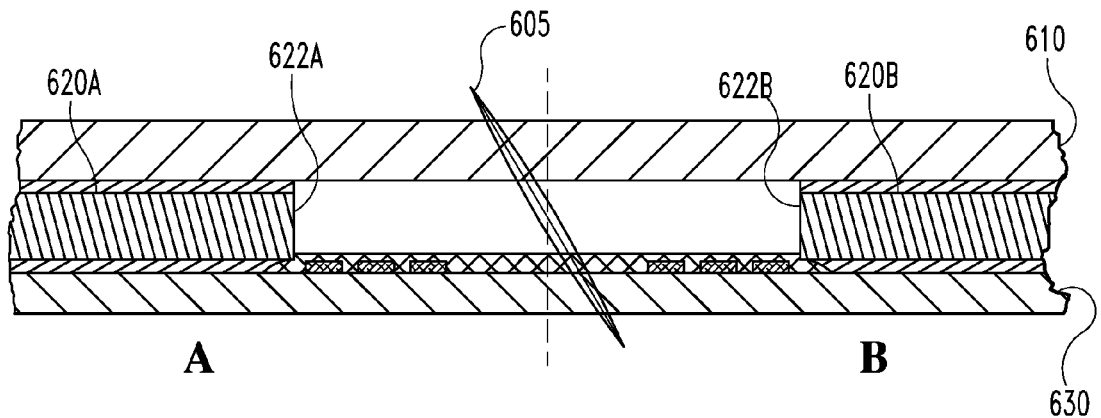
FIG. 43 is a fragmentary, cross sectional view of a single-cut singulation process for providing disparate overhang distances for the top layer and bottom layer substrates.

In the embodiment depicted in FIG. 41, the electrode patterns (which include contact pad patterns 512A and sampling end electrode patterns 514A) are arranged perpendicularly to the longitudinal axis 542. Two elongated spacer layer tapes 550A are applied to the top of the electrode patterns and the elongated lower substrate 540. The elongated spacer layer tapes 550A include straight (linear) sides, and do not require ratchet cutting. As such, the sample chambers formed when the upper substrate layer is applied are not rectangular, but rather triangular or trapezoidal depending on the location of edge 551. As such, the cantilever overhang of the upper and lower substrate layers varies across the width of the test strip and sample chamber. However, in alternate embodiments such as the one illustrated in FIG. 42, the edges 551 of the elongated spacer tape 550A adjacent the electrode patterns 514A are ratcheted to produce test chambers where the cantilever overhang of the upper and lower substrate layers are constant across the width of the test strip and sample chamber, i.e., the sample chambers are parallelogram-shaped.

During the singulation process when the individual test strips are separated from one another, a ratchet cut is used to form the sampling ends of the test strips and to separate the two adjacent columns of test strips. An exemplary embodiment of a single strip singulated in this manner is shown in FIG. 39 corresponding to the web of FIG. 41, and shown in FIG. 40 corresponding to the web of FIG. 42.

Figure 47:
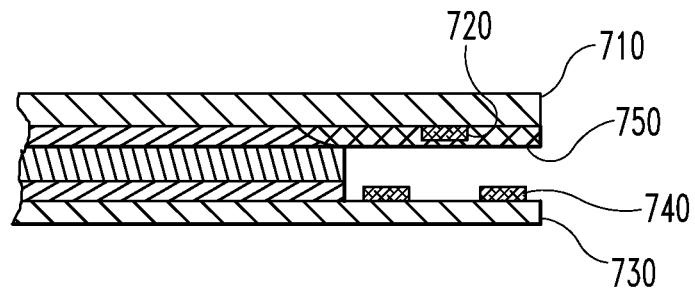
FIG. 47 is a fragmentary, cross sectional view of an alternative embodiment of a biosensor according to the present invention having a facing electrode configuration.

Referring now to FIGS. 47 and 48, further embodiments of a single-use biosensor having a FWED capillary chamber are shown having facing electrode configurations rather than coplanar configurations. In FIG. 47, the facing surfaces of the bottom layer 730 and the top layer 710 are formed with the counter electrode 740 and working electrode 720 patterns, respectively. The reagent layer 750 is provided in connection with the working electrode 720. In such embodiments, the surfaces of both the top layer 710 and the bottom layer 730 are metalized and then the appropriate respective electrode pattern is formed to include only one of the counter electrode 740 and working electrode 720. Other electrodes such as dose detection or sample sufficiency electrodes may be additionally provided as desired in accordance with the discussions hereinabove.

In FIG. 48, rather than forming specific patterns for the electrodes, the surfaces are simply left fully metalized such that the one entire surface comprises a working electrode 820 and the other entire surface comprises a counter electrode 840. In this particular embodiment, any variability in the placement of the spacer layer 830 relative to the end of the strip 850 is mitigated similarly as described previously because, although the effective (exposed) area of the working electrode that is increased or decreased as a result of that variability is slightly larger than with a thin neck leading to a specifically formed or patterned working electrode (such as in FIG. 5), the overall area of the working electrode is significantly larger and thus the variability impacts the effective area to a lesser degree. In yet other embodiments (not shown), the layer comprising the counter electrode may be partially patterned in order to include other electrical pattern structures as desired, such as dose detection and/or sample sufficiency electrodes.

In the embodiments of FIGS. 47 and 48, the connector end of the strip comprises contact pads or locations that are similarly facing. An appropriate connector in a meter corresponding to such biosensors is provided accordingly, the design of which is well within the abilities of a person of ordinary skill in the art. Similarly reconfigured connectors in meters would also be provided with regard to the biosensor embodiments of FIGS. 20-25.

As suggested with regard to FIGS. 24 and 25, FIGS. 47 and 48 also make it more straightforward to provide a biosensor having different materials for the different electrodes. For example, with regard to FIG. 48, the counter electrode 840 may actually comprise a reference electrode of ink jet deposited Ag/AgCl, whereas the working electrode 820 may comprise, e.g., a gold layer deposited typically using atomic vapor deposition methods.

While illustrated examples, representative embodiments and specific forms of the invention have been illustrated and described in detail in the drawings and foregoing description, the same is to be considered as illustrative and not restrictive or limiting. The description of particular features in one embodiment does not imply that those particular features are necessarily limited to that one embodiment. Features of one embodiment may be used in combination with features of other embodiments as would be understood by one of ordinary skill in the art, whether or not explicitly described as such. Dimensions, whether used explicitly or implicitly, are not intended to be limiting and may be altered as would be understood by one of ordinary skill in the art. Only exemplary embodiments have been shown and described, and all changes and modifications that come within the spirit of the invention are desired to be protected.

What is claimed is:

1. A method, comprising:
    forming electrode patterns on a substrate defining first and second columns of the electrode patterns oriented in a head-to-head manner;
    depositing a reagent material on the substrate that at least partially covers electrode patterns of each of the first and second columns;
    laminating a first spacer layer on top of the substrate and partially covering the first column;
    laminating a second spacer layer on top of the substrate and partially covering the second column, wherein the first and second spacer layers are spaced apart and define a gap therebetween exposing the portions of the electrode patterns covered by the reagent material;
    laminating a cover layer on top of the first and second spacer layers and spanning the gap;
    cutting the substrate and the cover layer at an angle at a location along the gap between the first and the second columns of the electrode patterns to form a first cantilever overhang portion of the cover layer, the first cantilever overhang portion of the cover layer spanning between a front edge of the cut cover layer and a front edge of the first spacer layer, and to form a second cantilever overhang portion of the cover layer, the second cantilever overhang portion of the cover layer spanning between a front edge of the cut cover layer and a front edge of the second spacer layer, wherein the first cantilever overhang portion of the cover layer has a length greater than the second cantilever overhang portion of the cover layer;
    cutting the substrate and the cover layer at a location between individual electrode patterns in the first and second columns of the electrode patterns to create a plurality of individual test strips; and
    wherein a capillary chamber is defined between the substrate and the cover layer, and between the first and second spacer layers.

2. The method of claim 1, wherein the forming the electrode patterns on the substrate includes positioning each of the first column of electrode patterns and the second column of electrode patterns perpendicular to a longitudinal axis of the substrate.

3. The method of claim 1, further comprising:
    forming a first cantilever overhang portion of the substrate, the first cantilever overhang portion of the substrate spans between a front edge of the cut substrate and a front edge of the first spacer layer; and
    forming a second cantilever overhang portion of the substrate, the second cantilever overhang portion of the substrate spans between a front edge of the cut substrate and a front edge of the second spacer layer.

4. The method of claim 3, wherein cutting at an angle forms the second cantilever overhang portion of the substrate with a length greater than a length of the first cantilever overhang portion of the substrate.

* * * * *